(12) United States Patent
Grubb et al.

(10) Patent No.: US 6,794,373 B2
(45) Date of Patent: Sep. 21, 2004

(54) CONTRACEPTIVE METHODS USING BENZIMIDAZOLONES

(75) Inventors: Gary S. Grubb, Newtown Square, PA (US); Puwen Zhang, Audubon, PA (US); Reinhold R. W. Bender, Valley Forge, PA (US); Jay E. Wrobel, Lawrenceville, NJ (US); James P. Edwards, San Diego, CA (US); Todd K. Jones, Solana Beach, CA (US); Christopher M. Tegley, Thousand Oaks, CA (US); Lin Zhi, San Diego, CA (US)

(73) Assignees: Wyeth, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 180 days.

(21) Appl. No.: 10/091,222

(22) Filed: Mar. 1, 2002

(65) Prior Publication Data

US 2002/0151531 A1 Oct. 17, 2002

Related U.S. Application Data

(62) Division of application No. 09/552,355, filed on Apr. 19, 2000
(60) Provisional application No. 60/198,249, filed on May 4, 1999.

(51) Int. Cl.$^7$ .................. A61K 31/56; A61K 31/54; A61K 31/535; A61K 31/4965; A61K 31/415
(52) U.S. Cl. ................. 514/171; 514/224.2; 514/230.5; 514/255.06; 514/390
(58) Field of Search .............. 514/171, 224.2, 514/230.5, 255.06, 390

(56) References Cited

U.S. PATENT DOCUMENTS

| | | |
|---|---|---|
| 3,635,964 A | 1/1972 | Skorcz |
| 3,917,592 A | 11/1975 | Kobzina |
| 4,093,730 A | 6/1978 | Butti |
| 4,440,785 A | 4/1984 | Walsh |
| 4,666,913 A | 5/1987 | Kubla |
| 4,670,566 A | 6/1987 | Walsh |
| 4,721,721 A | 1/1988 | Kuhla |
| 4,822,794 A | 4/1989 | Spada |
| 4,831,027 A | 5/1989 | Narr |
| 4,853,473 A | 8/1989 | Fischer |
| 5,007,952 A | 4/1991 | Kume |
| 5,171,851 A | 12/1992 | Kim |
| 5,414,088 A | 5/1995 | Von Der Saal |
| 5,453,516 A | 9/1995 | Fischer |
| 5,475,020 A | 12/1995 | Johnson |
| 5,521,166 A | 5/1996 | Grubb |
| 5,681,817 A | 10/1997 | Hodgen |
| 5,688,808 A | 11/1997 | Jones |
| 5,688,810 A | 11/1997 | Jones |
| 5,693,646 A | 12/1997 | Jones |
| 5,693,647 A | 12/1997 | Jones |
| 5,696,127 A | 12/1997 | Jones |
| 5,696,130 A | 12/1997 | Jones |
| 5,696,133 A | 12/1997 | Jones |
| 5,719,136 A | 2/1998 | Chwalisz |
| 5,733,902 A | 3/1998 | Schneider |
| 5,767,131 A | 6/1998 | Gluchowski |
| 5,808,139 A | 9/1998 | Pathirana |
| 5,874,430 A | 2/1999 | Christ |
| 6,077,840 A | 6/2000 | Kurihara |
| 6,306,851 B1 | 10/2001 | Santilli |
| 6,319,912 B1 | 11/2001 | Grubb |
| 6,329,416 B1 | 12/2001 | Grubb |
| 6,339,098 B1 | 1/2002 | Collins |
| 6,355,648 B1 | 3/2002 | Fensome |
| 6,358,947 B1 | 3/2002 | Zhi |
| 6,358,948 B1 | 3/2002 | Zhang |
| 6,369,056 B1 | 4/2002 | Zhang |

FOREIGN PATENT DOCUMENTS

| | | |
|---|---|---|
| DE | 3633861 | 4/1988 |
| DE | 4330234 | 3/1995 |
| DE | 4344463 | 6/1995 |
| EP | 022317 | 1/1981 |

(List continued on next page.)

OTHER PUBLICATIONS

R. Evans, "The Steroid and Thyroid Hormone Receptor Superfamily", Science, 240:889 (May 13, 1988).

(List continued on next page.)

*Primary Examiner*—Sreeni Padmanabhan
*Assistant Examiner*—San-ming Hui
(74) *Attorney, Agent, or Firm*—Howson and Howson

(57) ABSTRACT

This invention relates to cyclic combination therapies and regimens utilizing indoline compounds which are antagonists of the progesterone receptor and having the general structure:

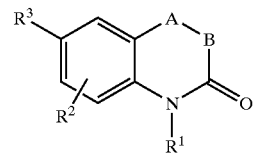

A is O, S, or NR$^4$; B is a bond or CR$^5$R$^6$;
R$^4$, to R$^6$ are H, C$_1$ to C$_6$ alkyl, C$_2$ to C$_6$ alkenyl, C$_2$ to C$_6$ alkynyl, C$_3$ to C$_8$ cycloalkyl, aryl, or heterocyclic, or R$^4$ and R$^5$ are fused to form a ring; R$^1$ is H, OH, NH$_2$, C$_1$ to C$_6$ alkyl, C$_3$ to C$_6$ alkenyl, alkynyl, or COR$^A$; R$^A$ is as defined; R$^2$ is H, halogen, CN, NO$_2$, C$_1$ to C$_6$ alkyl, C$_1$ to C$_6$ alkoxy, or C$_1$ to C$_6$ aminoalkyl; R$^3$ is a substituted benzene ring, or heteroaromatic ring, in combination with a progestational agent and/or an estrogen to treat or prevent secondary amenorrhea, dysfunctional bleeding, uterine leiomyomata, endometriosis, polycystic ovary syndrome, carcinomas and adenocarcinomas, and contraception, among others.

26 Claims, No Drawings

FOREIGN PATENT DOCUMENTS

| | | |
|---|---|---|
| EP | 208510 | 1/1987 |
| EP | 311135 | 4/1989 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63112584 | 5/1988 |
| WO | WO86/03749 A1 | 7/1986 |
| WO | WO91/04974 A1 | 4/1991 |
| WO | WO91/06545 A1 | 5/1991 |
| WO | WO93/12085 A1 | 6/1993 |
| WO | WO94/14434 A1 | 7/1994 |
| WO | WO94/29272 A1 | 12/1994 |
| WO | WO95/11013 A1 | 4/1995 |
| WO | WO95/20389 A1 | 8/1995 |
| WO | WO95/20972 A1 | 8/1995 |
| WO | WO95/33746 A1 | 12/1995 |
| WO | WO96/15794 A1 | 5/1996 |
| WO | WO96/19458 A1 | 6/1996 |
| WO | WO96/19997 A1 | 7/1996 |
| WO | WO97/13767 A1 | 4/1997 |
| WO | WO97/49407 A1 | 12/1997 |
| WO | WO98/14436 A1 | 4/1998 |
| WO | WO98/27059 A1 | 6/1998 |
| WO | WO98/55116 A1 | 12/1998 |
| WO | WO99/10325 A1 | 3/1999 |
| WO | WO99/11264 A1 | 3/1999 |
| WO | WO99/15500 A1 | 4/1999 |
| WO | WO99/44608 A1 | 9/1999 |

OTHER PUBLICATIONS

A. Ulmann et al, "Clinical Uses of Mifepristone (MFP)", Ann. N.Y. Acad. Sci., 261:248 (Jun. 12, 1995).

R. Kekkonen et al, "Sequential Regiment of the Antiprogasterone RU486 and Synthetic Progestin for Contraception", Fertility and Sterility, 60(4):610 (Oct., 1993).

K. Horwitz et al, "Progestin, Progesterone Receptors, and Breast Cancer", Horm. Cancer, publisher: Birkhaeuser, Boston, Mass, ed. Vedeckis, pp. 283–306 (1996) (abstract only).

A. Murphy et al, "Regression of Uterine Leiomyomata in Response to the Antiprogesterone RU486", J. Clin. Endo. Metab., 76(2):513 (Feb., 1993).

L. Kettel et al, "Endocrine Responses to Long–Term Administration of the Antiprogesterone RU486 in Patients with Pelvic Endometriosis", Fertility and Sterility, 56(3):402 (Sep., 1991).

H. Michna et al, "Differentiation Therapy with Progesterone Antagonists", Ann. N.Y. Acad. Sci., 761:224 (Jun., 1995).

L. Zhi et al, "5–Aryl–1,2–Dihydrochromeno[3,4–f]quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High–Affinity Ligands with Selectivity for Bone Cell Progesterone Receptors", J. Med. Chem., 38:4880 (Dec. 8, 1995).

K. Perlman et al, "20–Oxopregnacalciferols: Vitamin D Compounds that Bind the Progesterone Receptor", Tet. Letters, 35(15)2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlzsepine Derivatives with Antiprogestin Activity", PQI–37, 16$^{th}$ Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effects of Brofoxine, A New Anxiolytic on Experimentally Induced Conflict in Rats", Proc. West Pharmacol. Soc., 21:51–55 (1978).

B. Singh et al, "Novel cAMP FDE III Inhibitor", Imidazo [4,5–b]pyridin–2(3H)–ones and Thiazolo[4,5–b]pyridin–2(3H)–ones and their Analogs, J. Med. Chem., 37:248 (Jan. 21, 1994).

A. Andreani et al, "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7–Chlor–5–phenyl–2–thioxo–1H–2,3–dihydro–1,3,4–benzotriazepinen", Pharmazie, 37(10):714–717 (1982).

E. Barengolts et al, "Progesterone Antagonists RU486 has Bone–Sparing Effects in Ovariectomized Rats", Bone, 17(1):21 (Jul., 1995).

E. Gromachevskaya et al, "Studies of 4H–3, 1–Benzoxazines", Chem. Heterocycl. Cmpda, 33(10):1209–1214 (1997).

D. Chiarino et al, "2,1–Benzisothiazoline 2,2–Dioxide and Derivatives", J. Heterocycl. Chem., 23(6):1645–1649 (Nov.–Dec., 1986).

A. Turck et al, "On the Metabolism of 3–Substituted and 3,6–Disubstituted Pyridazines", Tetrahedron, 49(3):599–606(1993).

V. Kumar et al, "Synthesis of 7–Azaindols and 7–Azaoxindols Derivatives through a Palladium–Catalyzed CrossCoupling Reaction", J. Org. Chem., 57(25):6995–6998, (1992).

P. Canonne et al, "Spirocyclization of 1–(o–Aminophenyl) cycloalkanols and 1–(2'–Amino–3'–pyridinyl)cycloalkanols", J Heterocyclic Chem., 26:113 (Jan.–Feb., 1989).

M–C. Forest et al, "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", J. Med. Chem., 35:163–172 (Jan., 1992).

D. Combs et al, "Heteroatom Analogues of Bemoradan: Chemistry and Cardiotonic Activity of 1,4–Benzothiazinylpyridazmones", J. Med. Chem., 35:172–176 (Jan., 1992).

Kurihari et al., "Synthesis of (*)–PF1092A, B, and C; New Nonsteroidal Progesterone Receptor Ligands", J. Antibiotics, 50(4):360 (Apr., 1997).

A. Kende et al., "Regioselective C–3 Alkylation of Oxindole Dianion", Synth. Commun. 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", J. Med. Chem., 37:2347–2444 (Jul. 22, 1994).

J. Edwards et al., "5–Aryl–1,2–Dihydro–5H–Chromeno[3, 4–f]Quinolines as Potent, Orally Active, Nonsteroidal Progesterone Receptor Agonists: The Effect of D–Ring Substituents", J. Med. Chem., 41:303–310 (Jan. 29, 1998).

Derwent WPI abstracts, "New Imidazo–Pyridine Derivatives—Useful as Platelet Agglutination Inhibitor, Antiallergic, Antiinflammatory Sedative, Cardiac, and Cardiovascular Vasodilators", JP 63112584, May, 1988.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850, Feb. 1990.

Derwent WPI abstract, F. Arndt et al., "New Heterocycle substituted Benzo–Fused Azine and Azole Derivatives—Useful as Selective Herbicides for Pre or Post–Emergence Application", EP 311135 Nov. 1988.

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

V. Mamaev et al., "Synthesis of 4H–Thieno [3,2–B] Pyrrol–5(6H)–One" Bulletin of the Academy of Sciences on the USSR Division of Chemical Science, US, Consultants Bureau. New York. vol. 9, p. 1549–1553, (1966).

Derwent WPI Abstract, K. Chwalisz et al. "Female Contraceptive Method Comprises Gestation Treatment with Intermittent Progesterone Antagonist Administration.", DE 4,330,234, Mar. 1995.

Derwent WPI Abstract, K. Chwalisz et al. "Contreceptive Pack for Implantation Inhibition—Contains Competitive Progesterone Antagonist and Gestagea for Sequential Oral Administration.", DE 4,344,463, Jun. 1995.

K. Kolasa et al., "Preliminary Pharmacological Studies of the Central Action of Phenyl and Piperidinomethyl Derivatives of 2–Benzoxazolone", Chemical Abstracts, vol. 99, No. 1, Abst. No. 157a (Jul. 4, 1983).

N. Meanwell et al., "Regiospecific Functionalization of 1,3–dihydro–2H–Benzimidazol–2–One and Structurally Related Cyclic Urea Derivatives", J. Organic Chem., 60(6):1565–82 Mar. 24, 1995.

B. Singh et al., "An Efficient and Novel Synthesis of Fused Thiazol–2(3H)–ones" Heterocycles, 36(1):133–134, p. 136, compounds 16a, 18a Jan. 1993.

G. Vernin et al., "Etude Dans la Sctic des Radicaux Heterocycliques. Partie XV, Decomposition aprotique de l' amino–6–ethyl–2–benzothiazole dans des substrats aromatiques et heteroaromatiques: preparation des memityl–6– et furyl–6–ethyl–2–benzothiazoles, des sels quaterernaires et des spiropyrannes correspondants", Helvetica Chimica Acta, 62(1/3):21–30 Jan. 24, 1979.

A. Schering et al, "Utilization of Progestine and Competitive Progesterone Antagonists for the Preparation of Medications for Female Fertility Control as Well as Substances Containing a Progestin and a Competitive Progesterone Antagonist", English Translation of German Patent No. DE 4330234, issued Mar. 9, 1995.

A. Schering et al, "Compound Product for Contraception", English Translation of German Patent No. DE4344463, issued Jun. 29, 1995.

CONTRACEPTIVE METHODS USING BENZIMIDAZOLONES

CROSS REFERENCE TO RELATED APPLICATIONS

This application is a divisional of U.S. patent application Ser. No. 09/552,355, filed Apr. 19, 2000, which claims the benefit of the priority of U.S. Provisional Patent Application No. 60/198,249, filed May 4, 1999, now abandoned.

BACKGROUND OF THE INVENTION

This invention relates to regimens of administering compounds which are antagonists of the progesterone receptor.

Intracellular receptors (IR) form a class of structurally related gene regulators known as "ligand dependent transcription factors" (R. M. Evans, *Science*, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, typically in the presence of an ER agonist. ER agonists are used to treat the symptoms of menopause, but have been associated with a proliferative effect on the uterus which can lead to an increased risk of uterine cancers. Co-administration of a PR agonist reduces/ablates that risk.

PR antagonists may also be used in contraception. In this context they may be administered alone (Ulmann, et al, *Ann. N.Y. Acad. Sci.*, 261, 248, 1995), in combination with a PR agonist (Kekkonen, et al, *Fertility and Sterility*, 60, 610, 1993) or in combination with a partial ER antagonist such as tamoxifen (WO 96/19997 A1 Jul. 4, 1996). PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, *J. Clin. Endo. Metab.*, 76, 513, 1993) and endometriosis (Kettel, et al, *Fertility and Sterility*, 56, 402, 1991). PR antagonists may also be useful in hormone replacement therapy for post menopausal patients in combination with a partial ER antagonist such as tamoxifen (U.S. Pat. No. 5,719,136). PR antagonists, such as mifepristone and onapristone, have been shown to be effective in a model of hormone dependent prostate cancer, which may indicate their utility in the treatment of this condition in men (Michna, et al, *Ann. N.Y. Acad. Sci.*, 761, 224, 1995).

Jones, et al, (U.S. Pat. No. 5,688,810) disclose the PR antagonist dihydroquinoline 1.

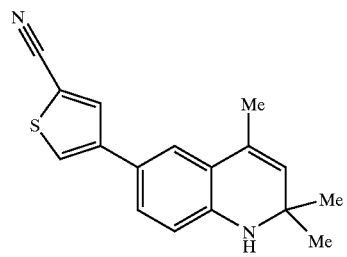

Jones, et al, described the enol ether 2 (U.S. Pat. No. 5,693,646) as a PR ligand.

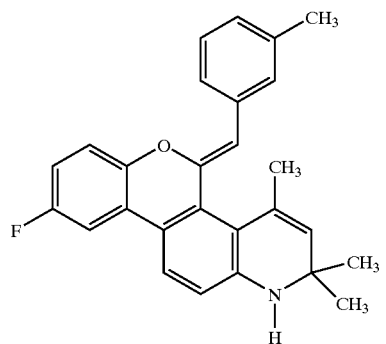

Jones, et al, described compound 3 (U.S. Pat. No. 5,696,127) as a PR ligand.

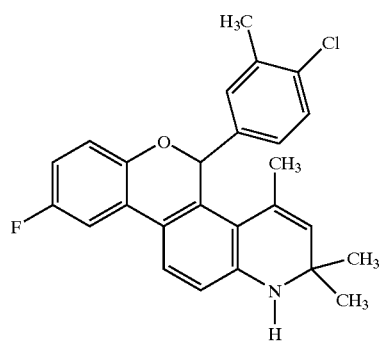

Zhi, et al, described lactones 4, 5 and 6 as PR antagonists (*J. Med. Chem.*, 41, 291, 1998).

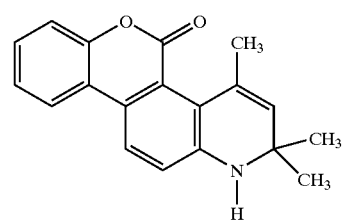

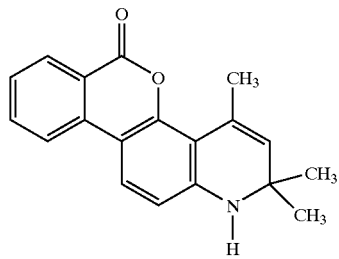

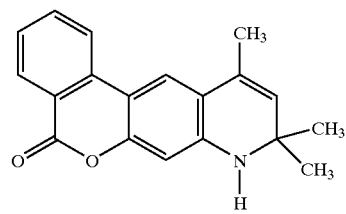

Zhi, et al, described the ether 7 as a PR antagonist (*J. Med. Chem.*, 41, 291, 1998).

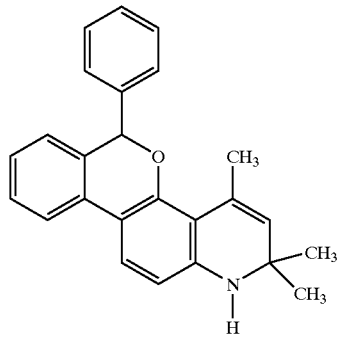

Combs, et al., disclosed the amide 8 as a ligand for the PR (*J. Med. Chem.*, 38, 4880, 1995).

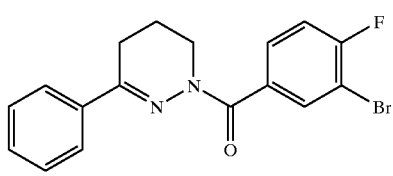

Perlman, et. al., described the vitamin D analog 9 as a PR ligand (*Tet. Letters*, 35, 2295, 1994).

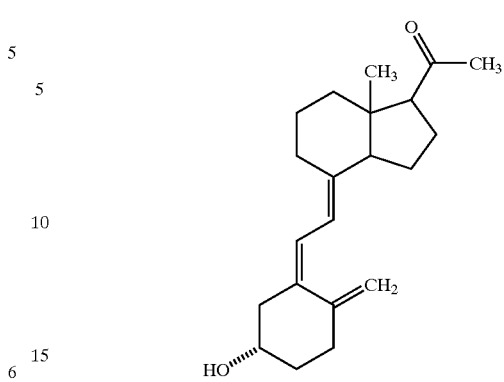

Hamann, et al, described the PR antagonist 10 (*Ann. N.Y. Acad. Sci.*, 761, 383, 1995).

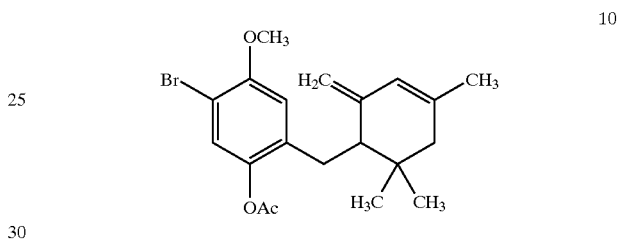

Chen, et al, described the PR antagonist 11 (Chen, et al, POI-37, 16th Int. Cong. Het. Chem., Montana, 1997).

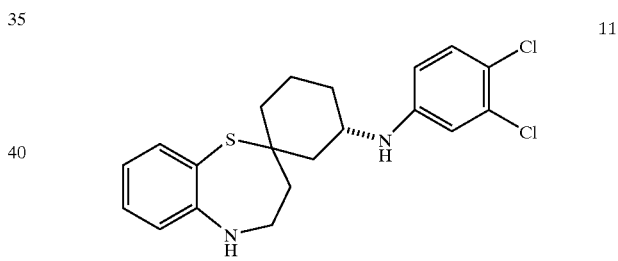

Kurihari, et. al., described the PR ligand 12 (*J. Antibiotics*, 50, 360, 1997).

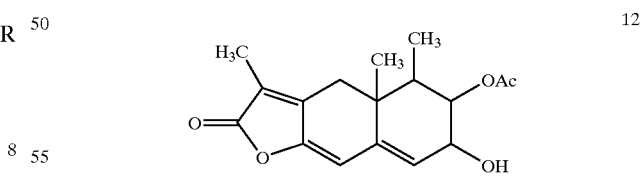

Among the examples of the prior art, Ueda et al. (EP 22317) claimed benzothiazoline and benzoxazoline compounds of formula A as the inhibitors of aldose reductase. The benzimidazolinone derivatives such as compound B were disclosed by Hara et al. (EP 454330) and claimed as lung surfactant secretion promoters. In their preparation of benzoimidazole and analogues as antiulcer and cardiovascular agents, Bru-Magniez et al. (EP 385850) synthesized the benzoimidazolinones such as compound C. Used as cAMP PDE III inhibitors, benzoimidazolinones, benzoxazolinones, and benzothiazolinones as shown in formula D were reported by Singh et al (*J. Med. Chem.*, 37, 248–254 (1994)).

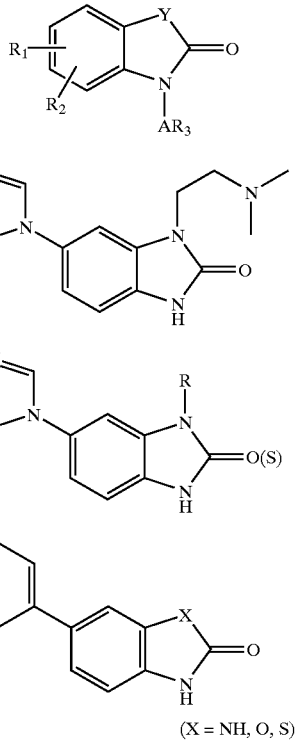

Related to quinoxalin-2-ones, European patent (Ganzer et al. EP 311135) discloses the compounds such as E as herbicides.

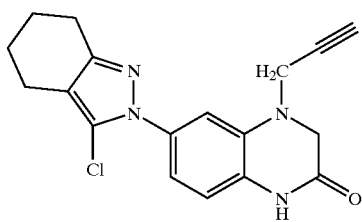

U.S. Pat. No. 5,521,166 (Grubb) teaches cyclophasic hormonal regimens comprising an antiprogestin and a progestin wherein the progestin is administered in the alternating presence and absence of an antiprogestin. The disclosed regimens also provide for use of an estrogen for a period of from 2–4 days to prevent breakthrough bleeding.

DESCRIPTION OF THE INVENTION

This invention provides combination therapies and dosing regimens utilizing antiprogestational agents in combination with one or more progestational agents. This invention further provides methods of treatment and dosing regimens further utilizing in combination with these antiprogestins and progestins, an estrogen, such as ethinyl estradiol.

These regimens and combinations may be administered to a mammal to induce contraception or for the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake. The uses herein for the treatment and/or prevention of the conditions or diseases described above includes the continuous administration or periodic discontinuation of administration of the invention to allow for minimization of effect dose or minimization of side effects or cyclic menstrual bleeding.

The use of this invention for contraception includes administration, preferably orally, to a female of child bearing age an antiprogestin in combination with an estrogen or progestin or both. These administration regimens are preferably carried out over 28 consecutive days, with a terminal portion of the cycle containing administration of no progestins, estrogens or anti-progestins.

The progestins of these combinations may be administered alone or in combination with an estrogen for the first 14 to 24 days of the cycle, the progestins being administered at a dosage range equal in progestational activity to about 35 μg to about 150 μg levonorgestrel per day, preferably equal in activity to from about 35 μg to about 100 μg levonorgestrel per day. An antiprogestin may then be administered alone or in combination with an estrogen for a period of 1 to 11 days to begin on any cycle day between day 14 and 24. The anti-progestin in these combinations may be administered at a dose of from about 2μg to about 50 μg per day and the estrogen may be administered at a dose of from about 10 μg to about 35 μg per day. In an oral administration, a package or kit containing 28 tablets will include a placebo tablet on those days when the antiprogestin or progestin or estrogen is not administered.

In a preferred embodiment of this invention, the progestins of this invention may be administered alone or in combination with estrogen for the initial 18 to 21 days of a 28-day cycle, followed by administration of an antiprogestin, alone or in combination with an estrogen, for from 1 to 7 days.

The estrogen to be used in the combinations and formulations of this invention is preferably ethinyl estradiol.

Progestational agents useful with this invention include, but are not limited to, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the preferred progestins for use in the combinations of this invention are levonorgestrel, gestodene and trimegestone.

Examples of orally administered regimens of this invention over a 28 day cycle include administration of a progestational agent solely for the first 21 days at a daily dose equal in progestational activity to from about 35 to about 100 μg of levonorgestrel. An antiprogestin compound of this invention may then be administered at a daily dose of from about 2 to 50 mg from day 22 to day 24, followed by no administration or administration of a placebo for days 25 to 28. It is most preferred that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 μg levonorgestrel, preferably equal in activity to from about 35 to about 100 μg levonorgestrel, with an estrogen, such as ethinyl estradiol, at a daily dose range of from about 10 to about 35 µg. This may be followed as described above with an antiprogestin administered at a daily dose of from about 2 to 50 mg from day 22 to day 24, followed by no administration or administration of a placebo for days 25 to 28.

Still another regimen within the scope of this invention will include coadministration from days 1 to 21 of a progestational agent, the progestational agent, preferably levonorgestrel, being administered at a daily dose equal in progestational activity to from about 35 to about 100 µg levonorgestrel, and an estrogen, such as ethinyl estradiol, at a daily dose range of from about 10 to about 35 µg. This will be followed on days 22 to 24 by coadministration of an antiprogestin (2 to 50 mg/day) and an estrogen, such as ethinyl estradiol, at a daily dose of from about 10 to about 35 µg. From day 25 to day 28, this regimen may be followed by no administration or administration of a placebo.

This invention also kits or packages of pharmaceutical formulations designed for use in the regimens described herein. These kits are preferably designed for daily oral administration over a 28-day cycle, preferably for one oral administration per day, and organized so as to indicate a single oral formulation or combination of oral formulations to be taken on each day of the 28-day cycle. Preferably each kit will include oral tablets to be taken on each the days specified, preferably one oral tablet will contain each of the combined daily dosages indicated.

According to the regimens described above, one 28-day kit may comprise:
a) an initial phase of from 14 to 21 daily dosage units of a progestational agent equal in progestational activity to about 35 to about 150 µg levonorgestrel, preferably equal in progestational activity to about 35 to about 100 µg levonorgestrel;
b) a second phase of from 1 to 11 daily dosage units of an antiprogestin compound of this invention, each daily dosage unit containing an antiprogestin compound at a daily dosage of from about 2 to 50 mg; and
c) optionally, a third phase of an orally and pharmaceutically acceptable placebo for the remaining days of the cycle in which no antiprogestin, progestin or estrogen is administered.

A preferred embodiment of this kit may comprise:
a) an initial phase of 21 daily dosage units of a progestational agent equal in progestational activity to about 35 to about 150 µg levonorgestrel, preferably equal in progestational activity to about 35 to about 100 µg levonorgestrel;
b) a second phase of 3 daily dosage units for days 22 to 24 of an antiprogestin compound of this invention, each daily dosage unit containing an antiprogestin compound at a daily dosage of from about 2 to 50 mg; and
c) optionally, a third phase of 4 daily units of an orally and pharmaceutically acceptable placebo for each of days 25 to 28.

Another 28-day cycle packaging regimen or kit of this invention comprises:
a) a first phase of from 18 to 21 daily dosage units of a progestational agent equal in progestational activity to about 35 to about 150 µg levonorgestrel, preferably equal in activity to from about 35 to about 100 µg levonorgestrel, and, as an estrogen, ethinyl estradiol at a daily dose range of from about 10 to about 35 µg; and
b) a second phase of from 1 to 7 daily dosage units of an antiprogestin of this invention at a daily dose of from about 2 to 50 mg; and
c) optionally, an orally and pharmaceutically acceptable placebo for each of the remaining 0–9 days in the 28-day cycle in which no progestational agent, estrogen or antiprogestin is administered.

A preferred embodiment of the kit described above may comprise:
a) a first phase of 21 daily dosage units of a progestational agent equal in progestational activity to about 35 to about 150 µg levonorgestrel, preferably equal in activity to from about 35 to about 100 µg levonorgestrel, and, as an estrogen, ethinyl estradiol at a daily dose range of from about 10 to about 35 µg; and
b) a second phase of 3 daily dosage units for days 22 to 24 of an antiprogestin administered at a daily dose of from about 2 to 50 mg; and
c) optionally, a third phase of 4 daily dose units of an orally and pharmaceutically acceptable placebo for each of days 25 to 28.

A further 28-day packaged regimen or kit of this invention comprises:
a) a first phase of from 18 to 21 daily dosage units, each containing a progestational agent of this invention at a daily dose equal in progestational activity to about 35 to about 150 µg levonorgestrel, preferably equal in activity to from about 35 to about 100 µg levonorgestrel, and ethinyl estradiol at a daily dose range of from about 10 to about 35 µg;
b) a second phase of from 1 to 7 daily dose units, each daily dose unit containing an antiprogestin of this invention at a concentration of from 2 to 50 mg; and ethinyl estradiol at a concentration of from about 10 to about 35 µg; and
c) optionally, an orally and pharmaceutically acceptable placebo for each of the remaining 0–9 days in the 28-day cycle in which no progestational agent, estrogen or antiprogestin is administered.

A preferred embodiment of the package or kit just described comprises:
a) a first phase of 21 daily dosage units, each containing a progestational agent of this invention at a daily dose equal in progestational activity to about 35 to about 150 µg levonorgestrel, preferably from about 35 to about 100 µg levonorgestrel, and ethinyl estradiol at a daily dose range of from about 10 to about 35 µg;
b) a second phase of 3 daily dose units for days 22 to 24, each dose unit containing an antiprogestin of this invention at a concentration of from 2 to 50 mg; and ethinyl estradiol at a concentration of from about 10 to about 35 µg; and
c) optionally, a third phase of 4 daily units of an orally and pharmaceutically acceptable placebo for each of days 25 to 28.

In each of the regimens and kits just described, it is preferred that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also preferred that the kits contain the placebo described for the final days of the cycle. It is further preferred that each package or kit comprise a pharmaceutically acceptable package having indicators for each day of the 28-day cycle, such as a labeled blister package or dial dispenser packages known in the art.

In this disclosure, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

Compounds of this invention which may be used as the anti-progestational agents in the kits, methods and regimens herein are those of the Formula 1:

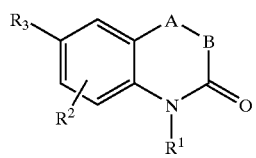

wherein:
A is O, S, or $NR^4$;
B is a bond between A and C=Q, or the moiety $CR^5R^6$;
$R^4$, $R^5$, $R^6$ are independently selected from H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, cyclic alkyl constructed by fusing $R^4$ and $R^5$ to from a 5 to 7 membered ring;
$R^1$ is selected from H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^A$;
$R^A$ is selected from H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^2$ is selected from H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^3$ is selected from a) or b):
a) $R^3$ is a trisubstituted benzene ring containing the substituents X, Y and Z as shown below:

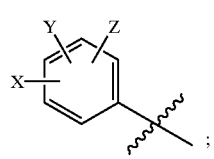

X is selected from the group of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^B$, $OCOR^B$, or $NR^CCOR^B$;
$R^B$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^C$ is H, $C_1$ to $C_3$ alkyl, or substituted $C_1$ to $C_3$ alkyl;
Y and Z are independent substituents taken from the group including H, halogen, CN, $NO_2$, $C_1$ to $C_3$ alkoxy, $C_1$ to $C_3$ alkyl, or $C_1$ to $C_3$ thioalkoxy; or
b) $R^3$ is a five or six membered ring with 1, 2, or 3 heteroatoms from the group including O S, SO, $SO_2$ or $NR^7$ and containing one or two independent substituents from the group of H, halogen, CN, $NO_2$ and $C_1$ to $C_3$ alkyl, $C_1$ to $C_3$ alkoxy, $C_1$ to $C_3$ aminoalkyl, $COR^D$, or $NR^ECOR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
$R^7$ is H, or $C_1$ to $C_3$ alkyl; or a pharmaceutically acceptable salt thereof.

Preferred anti-progestational compounds of this invention include those of the general formula described above wherein:
A is O, S, or $NR^4$;
B is a bond between A and C=Q, or the moiety $CR^5R^6$;
$R^4$, $R^5$, $R^6$ are independent substituents from the group including H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, or cyclic alkyl constructed by fusing $R^4$ and $R^5$ to from a 5 to 7 membered ring;
$R^1$ is H, OH, $NH_2$, $C_1$ to $C_6$ alkyl, substituted $C_1$ to $C_6$ alkyl, or $COR^A$;
$R^A$ is H, $C_1$ to $C_4$ alkyl, $C_1$ to $C_4$ alkoxy;
$R^2$ is H, halogen, $NO_2$, $C_1$ to $C_3$ alkyl, or substituted $C_1$ to $C_3$ alkyl;
$R^3$ is a disubstituted benzene ring containing the substituents X and Y as shown below

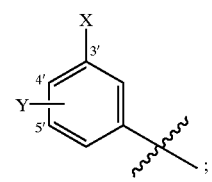

X is taken from the group of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;
Y is a substituent on the 4' or 5' position from the group of H, halogen, CN, $NO_2$, $C_1$ to $C_3$ alkoxy, $C_1$ to $C_4$ alkyl, or $C_1$ to $C_3$ thioalkoxy; or
$R^3$ is a five membered ring with the structure:

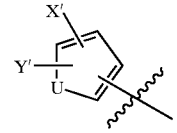

wherein:
U is O, S, or $NR^7$;
$PR^7$ is H, $C_1$ to $C_3$ alkyl, or $C_1$ to $C_4$ $CO_2$alkyl;

X' is selected from the group of halogen, CN, $NO_2$, $C_1$ to $C_3$ alkyl or $C_1$ to $C_3$ alkoxy;

Y' is H or $C_1$ to $C_4$ alkyl; or $R^3$ is a six membered ring with the structure:

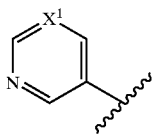

$X^1$ is N or $CX^2$;

$X^2$ is halogen, CN or $NO_2$;

or a pharmaceutically acceptable salt thereof.

Another preferred progesterone receptor antagonist subgroup of this invention comprises compounds of the general formula:

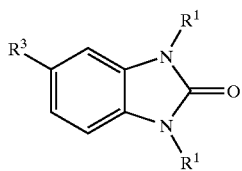

wherein:

$R^1$ is selected from H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^A$;

$R^A$ is selected from H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, benzyl, or substituted benzyl; and $R^3$ is selected from halogen or a disubstituted benzene ring containing the substituents X and Y as shown below

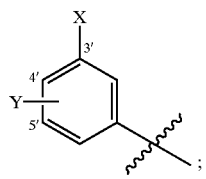

X is taken from the group of halogen, CN, $C_1$ to $C_3$ alkoxy, $C_1$ to $C_3$ alkyl, $NO_2$, $C_1$ to $C_3$ perfluoroalkyl, or $C_1$ to $C_3$ thioalkoxy;

Y is a substituent on the 4' or 5' position from the group of H, halogen, CN, $NO_2$, $C_1$ to $C_3$ alkoxy, $C_1$ to $C_4$ alkyl, or $C_1$ to $C_3$ thioalkoxy;

or a pharmaceutically acceptable salt thereof.

The anti-progestational compounds of this invention may contain an asymmetric carbon atom and some of the compounds of this invention may contain one or more asymmetric centers and may thus give rise to optical isomers and diastereomers. While shown without respect to stereochemistry in Formula I, II, and III, the present invention includes such optical isomers and diastereomers of these compounds; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having one to eight carbon atoms, preferably one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl group with at least one carbon-carbon triple bond and two to eight carbon atoms, preferably two to six carbon atoms.

The terms "substituted alkyl", "substituted alkenyl", and "substituted alkynyl" refer to an alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but are not limited to phenyl, naphthyl, biphenyl, anthryl, tetrahydronaphthyl, and phenanthryl. The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio. The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S ators may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl. The term "substituted heterocyclic" is used herein to describe the heterocyclic just defined having one to four substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio.

The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atorm The term "halogen" refers to Cl, Br, F, or I.

The anti-progestin compounds of the present invention can be prepared as described in the following schemes:

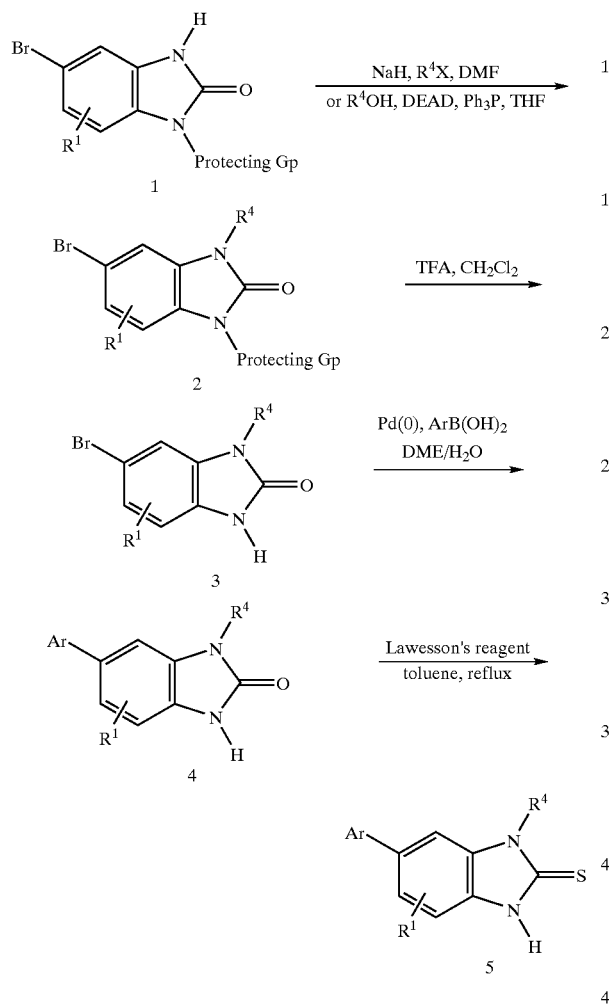

As illustrated in Scheme I, these compounds are generally prepared by employing the suitable coupling reaction as a final step and further converted to the thiourea analogues. Thus, an appropriately protected benzoimidazolinones 1 (numerous protecting groups including but not limited to alkyloxycarbonyl such as BOC group can be employed in the starting material 1) readily prepared according to the procedure of Meanwell et al. (*J. Org. Chem.* 60, 1565–1582 (1995)) can be alkylated at position-3 under a number of conditions. Among the reaction protocols, compound 1 can be alkylated by treatment of 1 with a suitable base such as sodium hydride in an appropriate nonprotic solvent such as DMF followed by addition of an alkylating agent such as alkyl iodide or triflate. Alternatively, the compound 2 can be effected employing a Mitsunobu protocol. The conventional Mitsunobu reaction can couple the compound 1 with an appropriate alcohol using a phosphorous reagent such as triphenyl phosphine and a dehydrating agent such as DEAD (diethyl azodicarboxylate) in a suitable solvent such as THF at the temperature ranging from 0° C. to the boiling point of the solvent which was employed. Deprotection of compound 2 to give 3 can be furnished via numerous conditions such as acidic deprotection using an acid such as neat trifluoroacetic acid or basic deprotection employing a base such as sodium alkoxide in a suitable solvent such as THF or alcohol at temperature ranging from ambient temperature to the boiling point of the solvent employed. The compounds of this invention, 4, can be readily prepared by employing various coupling reactions including Suzuki Stille protocols. These reactions are commonly performed in the presence of transition metallic catalyst, e.g., palladium or nickel complex often with phosphino ligands, e.g., Ph$_3$P, 1,1'-bis(diphenylphosphino)ferrocene, 1,2-bis(diphenylphosphino)ethane or a catalyst such as palladium acetate. Under this catalytic condition, an appropriately substituted nucleophilic reagent, e.g., aryl boronic acid, arylstannane, or aryl zinc compound, is coupled with bromobenzoimidazolinones 3 to give compounds 4. An appropriate base is often needed in the reaction; the commonly used bases include but not limited to sodium bicarbonate, sodium carbonate, potassium phosphate, barium carbonate, cesium fluoride, or potassium acetate. The most commonly used solvents in these reactions include benzene, DMF, isopropanol, ethanol, DME, ether, acetone or a mixture of above solvent and water. The coupling reaction is generally executed under an inert atmosphere such as nitrogen or argon at temperatures ranging from room temperature to 95° C.

The anti-progestin compounds of this invention, 5, can be easily prepared using an appropriate sulfur reagent such as Lawesson's reagent or P$_2$S$_5$ in a suitable solvent such as toluene, xylene, chlorobenzene at reflux under an inert atmosphere such as nitrogen or argon.

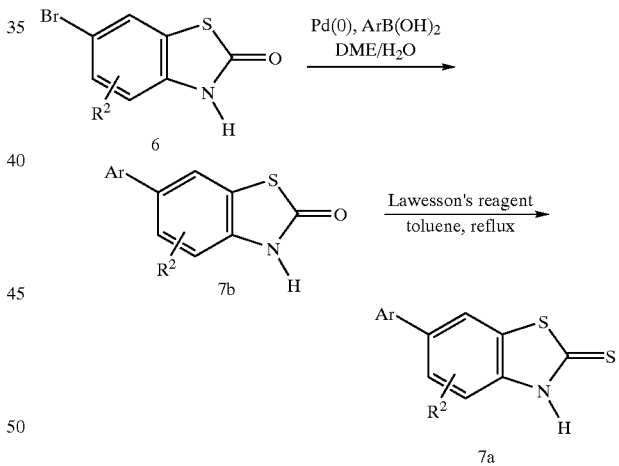

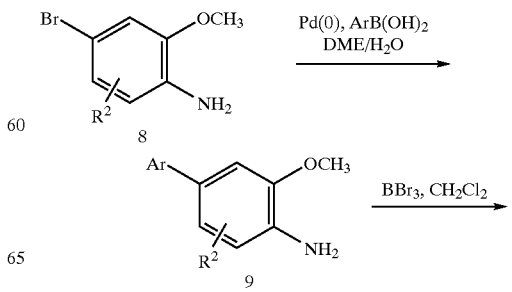

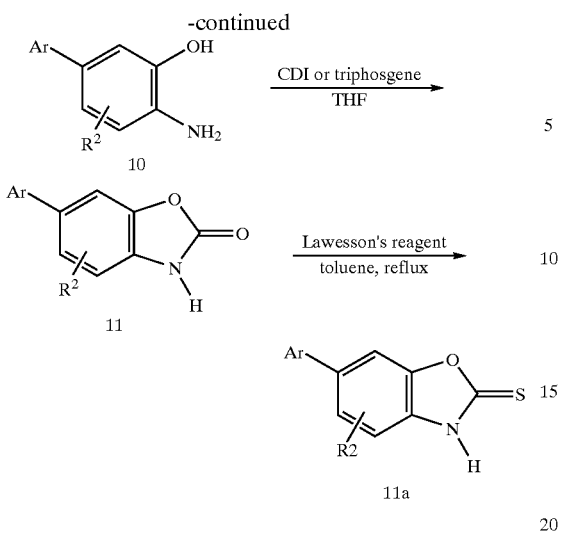

As shown in Scheme II, 5-aryl benzothiazolinones 7 can be readily effected from an appropriate 5-bromo-benzothiazolinone 6 and a suitable electrophile such as an aryl boronic acid, aryl tin reagent, or aryl zinc reagent via a suitable coupling reaction as described for the synthesis of benzimidazolinones 4. Conversion of 7b into 7a can be effected using an appropriate sulfur reagent such as Lawesson's reagent or $P_2S_5$ in a suitable solvent such as toluene, xylene, chlorobenzene at reflux under an inert atmosphere such as nitrogen or argon.

The synthetic approaches leading to the 5-aryl benzoxazolinones 11 are described in scheme III. As illustrated in scheme III, an appropriately substituted bromo o-anisidine can be coupled with an appropriate electrophile such as aryl boronic acid or aryl tin reagent via a coupling reaction as described for the synthesis of compounds 4 to give the biaryl 9. Demethylation of biaryl 9 to give amino phenol 10 can be furnished via various conditions including treatment of 9 with strong Lewis acid such as boron tribromide in a suitable solvent such as methylene chloride or treatment of 9 with a mixture of a suitable Lewis acid such as aluminum chloride and a soft nucleophile such as thiol in a suitable solvent such as methylene chloride under an inert atmosphere such as argon or nitrogen. Ring closure of amino phenol 10 to produce the compounds of this invention 11 can be effected by using a appropriate condensing agent such as carbonylduinidazole, phosgene, dimethylcarbonate, or diethylcarbonate in a suitable nonprotic solvent such as THF at temperatures ranging from room temperature to 65° C. Conversion of 11 into 11a can be accomplished using an appropriate sulfur reagent such as Lawesson's reagent or $P_2S_5$ in a suitable solvent such as toluene, xylene, chlorobenzene at reflux under an inert atmosphere such as nitrogen or argon.

Schemes IV, V, and VI describe the synthesis of other 5-aryl benzoimidazolinone, 5-aryl benzothiazolinone, 5-aryl benzoxazolinone bioisosteres. Using a similar procedure reported by Kondo et al. (Kondo, et al. *J. Med. Chem.* 33(7), 2012–2015(1990)) compound 12, 15, or 18 can be effected by treatment of compound 10, 14, or 17 with an appropriate ketene-S, S-acetals (at least one of $R_2$ or $R_3$ is an electron withdrawing group.) in a suitable solvent such as toluene or anhydrous ethanol under an inert atmosphere such as nitrogen or argon at reflux. In a similar fashion, compound 13, 16, or 19 can be accomplished by reaction of compound 10, 14, or 17 with an appropriate imino-S, S-acetals or imino-acetals ($R_2$ is an electron withdrawing group.) employing a procedure similar to that of Evers, et al. (Evers, et al. *I. Prakt. Chem.* 333(5), 699–710 (1991)) or Haake et al. (Haake et al. *Synthesis-Stuttgart* 9, 753–758 (1991)) in a suitable solvent such as ethanol under an inert atmosphere such as argon or nitrogen at reflux.

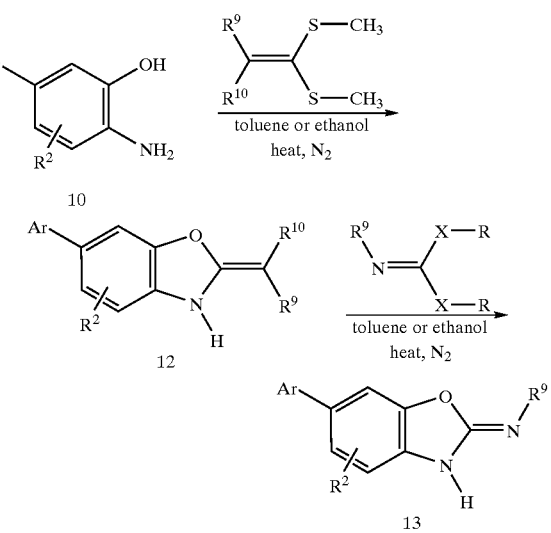

Compounds 14 and 17 can be prepared as shown in schemes V and VI from compound 4 and 7 using a strong basic condition such as heating the compound in a mixture of potassium hydroxide and ethylene glycol at 165° C. under an inert atmosphere such as argon or nitrogen.

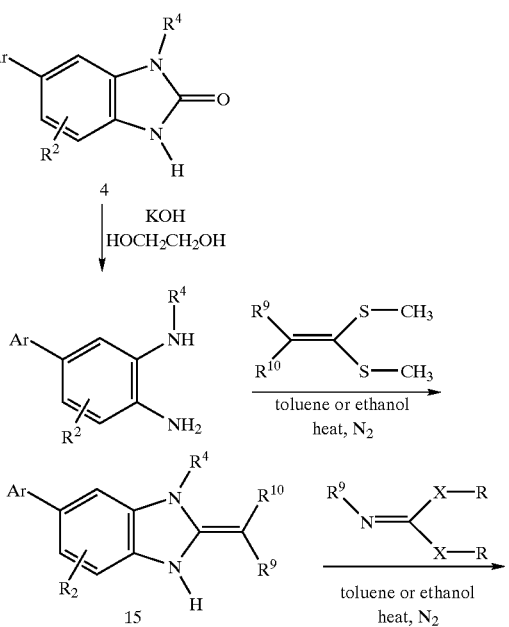

Scheme VII

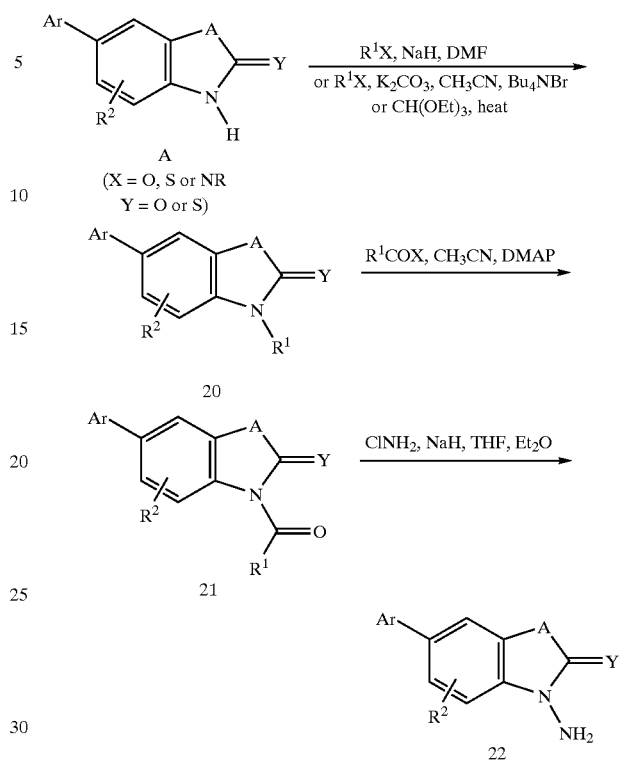

The acylation or carboxylation of the compound A at position-1 to give compound 21 can be readily effected by treatment of A with a suitable acylating or carboxylating reagent such as di-t-butyl dicarbonate in the presence of a suitable basic catalyst such as DMAP in a suitable solvent such as acetonitrile under an inert atmosphere such as argon or nitrogen. The amination of position-1 of compound A to give compound 22 can be furnished using a suitable aminating reagent such as chloroamine in the presence of a suitable base such as sodium hydride in a suitable solvent such as THF or diethyl ether following the literature procedure (Metlesics et al. *J. Org. Chem.* 30, 1311(1965)).

Scheme VI

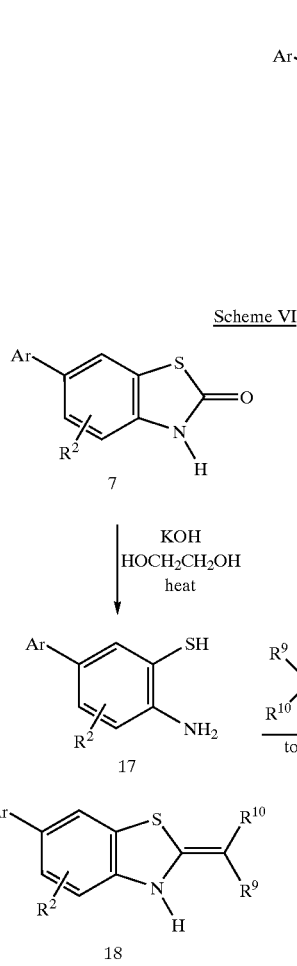

As illustrated in Scheme VII, the compounds of this invention can be further derivatized at position-1 via numerous approaches leading to a variety of the novel derivatives including 20, 21, and 22. Thus, alkyl or substituted alkyl derivatives 20 can be effected by treatment of compound A with a suitable base such as sodium hydride in suitable solvent such as DMF under an inert atmosphere such as argon or nitrogen followed by addition of an appropriate electrophile such as alkyl or substituted alkyl bromide, iodide, or triflate. Such transformation of A at position-1 can also be effected using a biphasic condition as indicated in Scheme VII in which alkylation is executed using a biphasic catalyst such as tributylammonium bromide in a suitable solvent such as acetonitrile. A further example of such modification includes, but is not limited to, the one depicted in Scheme VIII in that heating of A with triethyl orthoformate affords 1-substituted derivatives 20.

Scheme VIII

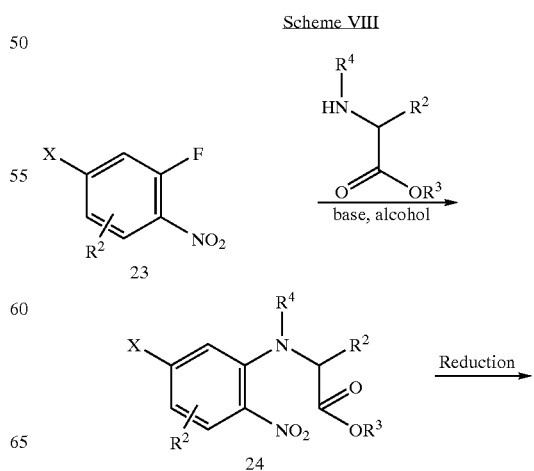

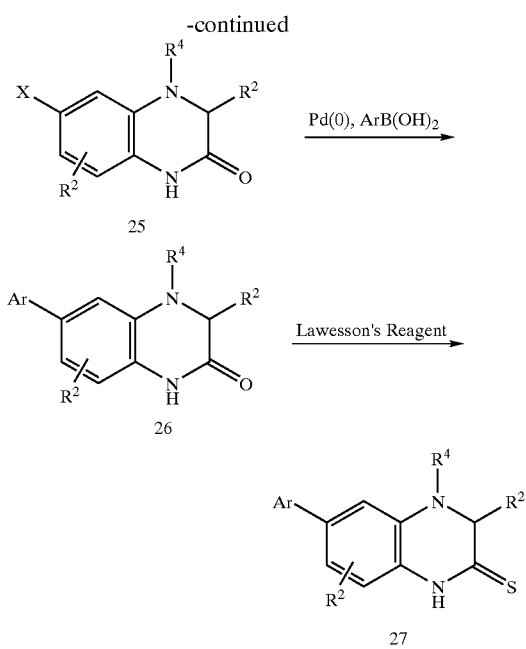

Scheme VIII describes a procedure to prepare quinoxalin-4-ones. An appropriately o-fluoro nitro-benzene 23 (X=I, Br, Cl) is reacted with an appropriate substituted amino acid derivatives in the presence of a suitable base in a protic solvent such as alcohol to give compound 24 which is readily reduced by a suitable reducing agent such as tin chloride to furnish quinoxalin-2-one 25. The anti-progestational compounds of this invention, 26, can be easily effected by coupling an appropriate aryl boronic acid with compound 25 in a similar fashion as for the preparation of compound 9. Conversion of 26 to 27 can be readily effected following the procedure of compound 11a.

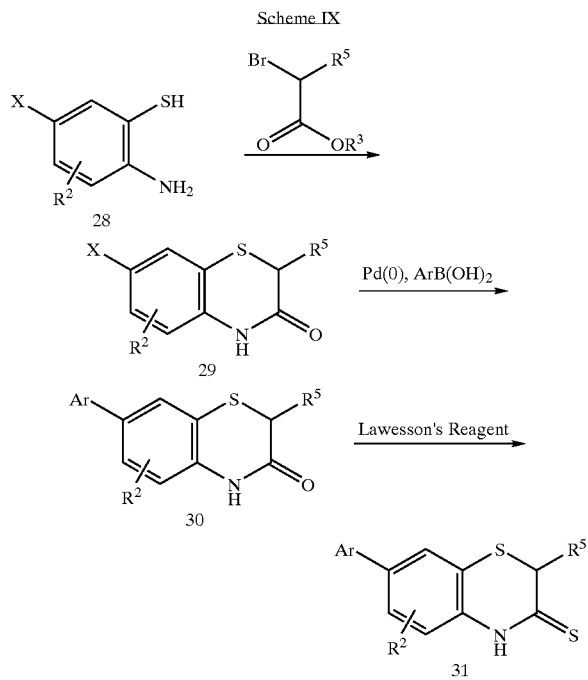

Scheme IX illustrates an approach to prepare the benzothiazinones. Thus, an appropriately substituted o-amino benzenethiol 28 is treated with an appropriately substituted α-bromoacetate in a suitable solvent such as ethanol to afford compound 29 which can be readily coupled with an appropriate aryl boronic acid following the protocol of compound 9 to afford the compounds of this invention, 30. Conversion of 30 to 31 can be carried out using a suitable sulfur reagent such as Lawesson's reagent according to procedure of compounds 11a.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium calcium or magnesium in the form of esters, carbamates and other conventional "prodrug" forms, which, when administered in such form, convert to the active moiety in vivo.

This invention includes pharmaceutical compositions comprising one or more compounds of this invention, preferably in combination with one or more pharmaceutically acceptable carriers and/or excipients. The invention also includes methods of contraception and methods of treating or preventing maladies associated with the progesterone receptor, the methods comprising administering to a mammal in need thereof a pharmaceutically effective amount of one or more compounds as described above wherein Q is oxygen as antagonists of the progesterone receptor. The invention further provides comparable methods and compositions which utilize one or more compounds herein wherein Q is S, $NR^6$, or $CR^7R^8$ as agonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

When used in contraception the progesterone receptor antagonists of the current invention may be used either alone in a continuous administration of between 0.1 and 500 mg per day, or alternatively used in a different regimen which would entail 2–4 days of treatment with the progesterone receptor antagonist after 21 days of a progestin. In this regimen between 0.1 and 500 mg daily doses of the progestin (e.g. levonorgestrel, trimegestone, gestodene, norethistrone acetate, norgestimate or cyproterone acetate) would be followed by between 0.1 and 500 mg daily doses of the progesterone receptor antagonists of the current invention.

The progesterone receptor antagonists of this invention, used alone or in combination, can also be utilized in methods of treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

The progesterone receptor agonists of this invention, used alone or in combination, can be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

When used in contraception the progesterone receptor agonists of the current invention are preferably used in combination or sequentially with an estrogen agonist (e.g. ethinyl estradiol). The preferred dose of the progesterone receptor agonist is between 0.01 and 500 mg per day.

This invention also includes pharmaceutical compositions comprising one or more compounds described herein, preferably in combination with one or more pharmaceutically acceptable carriers or excipients. When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The following non-limiting examples illustrate preparation and use of the compounds of the invention.

EXAMPLES

Example 1

5-Bromo-2-oxo-2,3-dihydro-benzoimidazole-1-carboxylic acid tert-butyl Ester

Prepared via a literature procedure (*J. Org. Chem.* 60(6), 1565–82 (1995)). White solid: mp 148–149° C.; $^1$H-NMR (DMSO-$d_6$) δ 11.4 (s, 1H), 7.6 (d, 1H, J=8.57 Hz), 7.2 (dd, 1H, J=8.57, 4.29 Hz), 7.1 (s, 1H), 1.6 (s, 9H); MS (ES) m/z 311([M−H]$^-$, 70%), 313 ([M−H]$^-$, 70%).

Example 2

1-Benzyl-6-bromo-1,3-dihydro-benzoimidazol-2-one

A mixture of 5-bromo-2-oxo-2,3-dihydro-benzoimidazole-1-carboxylic acid tert-butyl ester (2.5 g, 8 mmol), benzyl bromide (1.2 mL, 10 mmol), potassium carbonate (1.38 g, 10 mmol), and potassium iodide (50 mg) in anhydrous acetonitrile was heated at 80° C. under nitrogen for 1 hour. The reaction mixture was cooled to room temperature and treated with a saturated aqueous ammonium chloride solution (30 mL) and ethyl acetate (50 mL). The organic layer was separated and the aqueous layer was extracted with ethyl acetate (3×30 mL). The combined organic layers were washed with brine (30 mL) and dried (MgSO$_4$). After removal of the solvent, the residue was taken up in trifluoroacetic acid (10 mL, neat) and the solution was stirred at room temperature under nitrogen for 10 minutes. The reaction solution was then treated with brine (30 mL) and ethyl acetate (50 mL). The organic layer was separated and dried (MgSO$_4$). After removal of the solvent, the residue was applied to a pad of silica gel to afford the title compound as white solid (1.89, 78%): mp 245–246° C.; $^1$H-NMR (DMSO-$d_6$) δ 11.2. (s, 1H), 7.37–7.27 (m, 6H), 7.13 (dd, 1H, J=8.25, 2.25 Hz), 6.95 (d, 1H, J=8.25 Hz), 5.0 (s, 2H); MS (ES) m/z 301([M−H]$^-$, 50%), 303([M−H]$^-$, 50%).

Example 3

5-Bromo-3-methyl-2-oxo-2,3-dihydro-benzoimidazole-1-carboxylic acid tert-butyl ester A mixture of 5-bromo-2-oxo-2,3-dihydro-benzoimidazole-1-carboxylic acid tert-butyl ester (4.0 g, 12.8 mmol), iodomethane (2.74 g, 9.2 mmol), and $K_2CO_3$ in $CH_3CN$ (60 mL) was stirred at room temperature under a blanket of nitrogen overnight. Upon completion of the reaction, ethyl acetate (200 mL) was added and the organic layer was washed with $H_2O$ (200 mL), dried over $Na_2SO_4$, and concentrated. The residue was purified via chromatography (silica gel, 25% ethyl acetate/hexane) to give 5-bromo-3-methyl-2-oxo-2,3-dihydro-benzoimidazole-1-carboxylic acid tert-butyl ester as a white solid: mp 98–99° C.; $^1$H-NMR (CDCl$_3$) δ 7.7 (d, 1H, J=8.5 Hz), 7.27 (bs, 2H), 7.09 (d, 1H, J=2 Hz), 3.4 (s, 3H), 1.7 (s, 9H); MS (ES) m/z 349([M+Na]$^+$, 20%), 351([M+Na]$^+$, 20%); Anal. Calc. For $C_{13}H_{15}BrN_2O_3$: C, 47.73, H, 4.62, N, 8.56. Found: C, 47.46, H, 4.5, N, 8.29.

Example 4

6-Bromo-1-methyl-1,3-dihydro-benzoimidazol-2-one

Prepared from 5-bromo-3-methyl-2-oxo-2,3-dihydro-benzoimidazole-1-carboxylic acid tert-butyl ester in the same fashion as that of Example 2. White solid: mp 237–238° C.; $^1$H-NMR (DMSO-d$_6$) δ 11.0 (s, 1H), 7.35 (d, 1H, J=1.58 Hz), 7.14 (dd, 1H, J=7.89, 1.58 Hz), 6.92 (d, 1H, J=7.89 Hz), 3.3 (s, 3H); MS (ES) m/z 227([M+H]$^+$, 50%), 229([M+H]$^+$, 50%); Anal. Calc. For $C_8H_7BrN_2O$: C, 42.32, H, 3.11, N, 12.34. Found: C, 42.35, H, 3.07 N, 11.89.

Example 5

1-Benzyl-6-(3-chloro-phenyl)-1,3-dihydro-benzoimidazol-2-one

A mixture of 1-benzyl-6-bromo-1,3-dihydro-benzoimidazol-2-one (0.75 g, 2.5 mmol), 3-chloro-phenyl boronic acid (0.4 g, 2.6 mmol), tetrakis(triphenylphosphine)-palladium (0) (0.23 g, 0.2 mmol), and potassium carbonate (0.72 g, 5.2 mmol) in toluene (15 mL) and $H_2O$ (8 mL) was subject to a blanket of nitrogen for 15 minutes at 50° C. and then heated to 85° C. for 1 hour. The reaction mixture was cooled to room temperature and ethyl acetate (100 mL) was added. The organic layer was washed twice with aqueous ammonium chloride (30 mL) and once with brine (30 mL), dried over magnesium sulfate and concentrated. After removal of the solvent, the residue was purified via chromatography (silica gel, 25% ethyl acetate/hexane) to give 1-benzyl-6-(3-chloro-phenyl)-1,3-dihydro-benzoimidazol-2-one as a white solid (0.134 g, 16%): mp 168–169° C.; $^1$H-NMR (DMSO-d$_6$) δ 11.0 (s, 1H), 7.66 (t, 1H, J=2.05 Hz), 7.58–7.5 (m, 1H), 7.45 (t, 2H, J=8.18 Hz), 7.37–7.22 (m, 7H), 7.08 (d, 1H, J=8.18 Hz), 5.1 (s, 2H); MS (ES) m/z 333([M–H]$^-$, 100%); Anal. Calc. For $C_{20}H_{15}ClN_2O$: C, 71.75, H, 4.52, N, 8.37. Found: C, 70.27, H. 4.56, N, 8.0.

Example 6

1-Benzyl-6-(3-nitro-phenyl)-1,3-dihydro-benzoimidazol-2-one

Prepared from 1-benzyl-6-bromo-1,3-dihydro-benzoimidazol-2-one and 3-nitro-phenyl boronic acid in the same fashion as that of Example 5. White solid: mp 202–203° C.; $^1$H-NMR (DMSO-d$_6$) δ 11.2 (s, 1H), 8.38 (t, 1H, J=1.97 Hz), 8.15 (dd, 1H, J=7.83, 1.97 Hz), 8.80 (d, 1H, J=7.83 Hz), 7.72 (t, 1H, J=7.83 Hz), 7.56 (bs, 1H), 7.43–7.22 (r, 6H), 7.13 (d, 1H, J=7.83 Hz), 5.1 (s, 2H); MS (ES) m/z 344([M–H]$^-$, 100%); Anal. Calc. For $C_{20}H_{15}N_3O_3 \cdot 0.25H_2O$: C, 68.66, H, 4.46, N, 12.01. Found: C, 68.42, H, 4.44, N, 11.77.

Example 7

1-Methyl-6-(3-nitrophenyl)-1,3-dihydro-benzoimidazol-2-one

Prepared from 1-methyl-6-bromo-1,3-dihydro-benzoimidazol-2-one and 3-nitro-phenyl boronic acid in the same fashion as that of Example 5. White solid: mp 264–265° C.; $^1$H-NMR (DMSO-d$_6$) δ 11.0 (s, 1H), 8.47 (t, 1H, J=1.5 Hz), 8.19–8.15 (m, 2H), 7.75 (t, 1H, J=8.25 Hz), 7.58 (d, 1H, J=1.5 Hz), 7.43 (dd, 1H, J=8.25, 1.5 Hz), 7.1 (d, 1H, J=8.25 Hz), 3.37 (s, 3H); MS (ES) m/z 268([M–H]$^-$, 50%); Anal. Calc. For $C_{14}H_{11}N_3O_3$: C, 62.45, H, 4.12, N, 15.61. Found: C, 61.48, H, 4.36 N, 14.75.

Example 8

6-(3-chloro-phenyl)-1-methyl-1.3-dihydro-benzoimidazol-2-one

Prepared from 1-methyl-6-bromo-1,3-dihydro-benzoimidazol-2-one and 3-chloro-phenyl boronic acid in the same fashion as that of Example 5. mp 219–220° C.; $^1$H-NMR (DMSO-d$_6$) δ 11.0 (s, 1H), 7.75 (bs, 1H), 7.65 (dd, 1H, J=7.5, 1.76 Hz), 7.49–7.44 (m, 2H), 7.39–7.32 (m, 2H), 7.06 (d, 1H, J=7.94 Hz), 3.35 (s, 3H); MS (ES) m/z 259([M+H]$^+$, 100%); Anal. Calc. For $C_{14}H_{11}ClN_2O$: C, 65, H, 4.29, N, 10.83. Found: C, 64.44, H, 4.36 N, 10.6.

Example 9

5-(3-Nitro-phenyl)-1,3-dihydro-benzoimidazol-2-one

Prepared from 5-bromo-1,3-dihydro-benzoimidazol-2-one and 3-nitro-phenyl boronic acid in the same fashion as that of Example 5. White solid: mp 324–325° C.; $^1$H-NMR (DMSO-d$_6$) δ 10.8 (s, 2H), 8.4 (m, 1H), 8.15 (d, 1H, J=7.5 Hz), 8.1 (d, 1H, J=7.5 Hz), 7.7 (t, 1H, J=7.5 Hz), 7.35 (d, 1H, J=7.5 Hz), 7.3 (s, 1H), 7.05 (d, 1H, J=7.5 Hz); MS (ES) m/z 254 ([M–H], 100%); Anal. Calc. For $C_{13}H_9N_3O_3$: C, 61.18, H, 3.55, N, 16.46. Found: C, 60.5, H, 3.69 N, 15.53.

Example 10

4-Amino-3'-nitro-biphenyl-3-ol

4-Amino-3-methoxy-3'-nitro-biphenyl was prepared from 4-bromo-2-methoxyaniline (*Synth. Commun.* 23(6), 855–9 (1993)) and 3-nitrophenyl boronic acid according to the procedure of Example 5. White solid: mp 167–168° C.; $^1$H-NMR (CDCl$_3$) δ 8.39 (t, 1H, J=1.97 Hz), 8.13–8.09 (m, 1H), 7.88–7.84 (m, 1H), 7.55 (t, 1H, J=8.0 Hz), 7.09 (dd, 1H, J=7.98, 1.94 Hz), 7.04 (d, 1H, J=1.89 Hz), 6.80 (d, 1H, J=8.04 Hz), 4.0 (s, 5H).

4-Amino-3-methoxy-3'-nitro-biphenyl was then stirred with boron tribromide in dichloromethane to give 4-amino-3'-nitro-biphenyl-3-ol as an orange solid: mp 175–176° C.; $^1$H-NMR (DMSO-d$_6$) δ 9.3 (s, 1H), 8.25 (bs, 1H), 8.05 (d, 1H, J=8.33 Hz), 7.95 (d, 1H, J=8.33 Hz), 7.66 (t, 1H, J=7.5 Hz), 7.06–7.02 (m, 2H), 6.70 (d, 1H, J=8.33 Hz), 4.9 (s, 2H); MS (ES) m/z 229 ([M–H]$^-$, 100%).

Example 11

6-(3-Nitro-phenyl)-3H-benzooxazol-2-one

A solution of 4-amino-3'-nitro-biphenyl-3-ol (0.115 g, 0.5 mmol) in dry THF (2.5 mL) was treated with a solution of 1,1'-carbonyldiimidazole (0.098 g, 0.6 mmol) in dry THF (2.5 mL). The reaction mixture was stirred at room temperature under a blanket of nitrogen for 6 hours. A precipitate formed, was collected and washed with methylene chloride (50 mL) to give 6-(3-nitro-phenyl)-3H-benzooxazol-2-one (0.095 g, 74%) as a white solid: mp 280–281° C.; $^1$H-NMR (DMSO-d$_6$) δ 11.7 (s, 1H), 8.43 (t, 1H, J=1.15 Hz), 8.2–8.13 (nm, 2l), 7.79–7.72 (m, 2H), 7.59 (dd, 1H, J=8.08, 2.31 Hz), 7.21 (d, 1H, J=8.08 Hz), MS (ES) m/z 255([M−H]$^-$, 100%); Anal. Calc. For C$_{13}$H$_8$N$_2$O$_4$: C, 60.94, H, 3.15, N, 10.93. Found: C, 59.95, H, 3.17 N, 10.77.

Example 12

6-(3-Nitro-phenyl)-3H-benzothiazol-2-one

A mixture of 6-bromo-2-benzothiazolinone (5.0 g, 21.7 mmol), 3-nitrophenyl boronic acid (5.0 g, 30.0 mmol), tetrakis(triphenylphosphine)-palladium (0) (1.73 g, 1.5 mmol), and potassium carbonate (8.0 g, 58.0 mmol) in toluene (100 mL), H$_2$O (20 mL), and ethanol (30 mL) was subject to a blanket of nitrogen for 15 minutes at 50° C. and then was heated at 85° C. for 24 hours. The reaction mixture was cooled to room temperature and ethyl acetate (100 mL) was added. The organic layer was washed with aqueous ammonium chloride (2×50 mL) and with brine (100 mL), dried over magnesium sulfate and concentrated. The residue was purified via chromatography (silica gel, 25% ethyl acetate/hexane) to give 6-(3-nitro-phenyl)-3H-benzothiazol-2-one as a brown solid (0.1 g, 1.8%): mp 276–277° C.; $^1$H-NMR (DMSO-d$_6$) δ 11 (s, 1H), 8.44 (t, 1H, J=2.7 Hz), 8.21–8.08 (nm, 3H), 7.78–7.69 (m, 2H), 7.24 (d, 1H, J=9.23 Hz); MS (ES) m/z 271 ([M−H]$^-$, 100%); Anal. Calc. For C$_{13}$H$_8$N$_2$O$_3$S 0.25 H$_2$O: C, 56.41, H, 3.10, N, 10.12. Found: C, 56.48, H, 3.11, N, 9.99.

Example 13

6-(3-Chloro-phenyl)-3H-benzothiazol-2-one

Prepared from 6-bromo-2-benzothiazolinone, 3-chlorophenyl boronic acid according to the procedure of example 12. A white solid: mp 195–196° C.; $^1$H-NMR (DMSO-d$_6$) δ 11.95 (s, 1H), 7.96 (d, 1H, J=1.17 Hz), 7.7 (t, 1H, J=1.76 Hz), 7.62–7.59 (m, 2H), 7.46 (t, 1H, J=7.65 Hz), 7.4–7.38 (m, 1H), 7.18 (d, 1H, J=8.24 Hz); MS (EI) m/z 261 (M+, 30%); Anal. Calc. For C$_{13}$H$_8$ClNOS.0.5H$_2$O: C, 57.67, H, 3.35, N, 5.17. Found: C, 57.98, H, 3.11, N, 4.98.

Example 14

7-(3-Nitro-phenyl)-4H-benzo[1,4]thiazin-3-one

A mixture of 2-amino-5-bromo-benzenethiol (20 g, 0.1 mol), ethyl bromoacetate (19 g, 0.1 mol), and sodium bicarbonate (8.8 g, 0.1 mol) in DMF (200 ml) was heated to reflux for 2 hours. The mixture was diluted with water and extracted with ethyl acetate (2×100 mL). The combined organic extracts were washed with water, then brine, dried (MgSO$_4$) and evaporated to obtain the crude 7-bromo-4H-benzo[1,4]thiazin-3-one (20 g, 82%). A small portion of sample was recrystallized from ethanol to afford pure 7-bromo-4H-benzo[1,4]thiazin-3-one: mp 212–213° C.; MS (EI) m/z 243/245 (M+).

A solution of 7-bromo-4H-benzo[1,4]thiazin-3-one (2 g, 8.2 mmol), 3-nitrophenyl boronic acid (2.72 g, 16.4 mmol), potassium carbonate (6.85 g, 49.2 mmol), and tetrakis (triphenylphosphine) palladium(0) (0.95 g, 0.82 mmol) in dimethoxyethane (100 ml), ethanol (25 ml), and water (25 ml) was heated to reflux for 6 hours. After cooling to room temperature, the mixture was diluted with water and extracted with EtOAc (3×50 mL). The combined organic extracts were washed with water, then brine, dried (MgSO$_4$) and evaporated to obtain crude 7-(3-nitro-phenyl)-4H-benzo [1,4]thiazin-3-one (0.15 g, 6%). Recrystallization of crude sample from EtOAc afforded the title compound: mp 290–292° C.; MS (EI) m/z 286 (M$^{30}$).

Example 15

2-Ethyl-7-(3-nitro-phenyl)-4H-benzo[1,4]-thiazin-3-one

To a mixture of 2-amino-5-bromo-benzenethiol (20 g, 0.1 mol) and cesium carbonate (33 g, 0.1 mol) in DMF (500 ml) at −35° C. was added dropwise 2-bromobutyrylbromide (23 g, 0.1 mol). The mixture was allowed to warm to room temperature, poured into ice/water, and extracted with CH$_2$Cl$_2$ (2×50 mL). The combined organic extracts were washed with water, then brine, dried (MgSO$_4$) and evaporated. The residue was purified by column chromatography (SiO$_2$, ethyl acetate:hexane/1:6) to afford 7-bromo-2-ethyl-4H-benzo[1,4]thiazin-3-one (3.7 g, 14%): mp 100° C.; MS (EI) m/z 271/273(M+).

A solution of 7-bromo-2-ethyl-4H-benzo[1,4]thiazin-3-one (2 g, 7.3 mmol), 3-nitrophenyl boronic acid (1.22 g, 7.3 mmol), potassium carbonate (3 g, 22 mmol), and tetrakis (triphenylphosphine)palladium(0) (0.84 g, 0.72 mmol) in dimethoxyethane (100 ml), ethanol (25 ml), and water (25 ml) was heated to reflux for 6 hours. After cooling to room temperature, the mixture was diluted with water and extracted with EtOAc (3×40 mL). The combined organic extracts were washed with water, then brine, dried (MgSO$_4$) and evaporated. The residue was recrystallized from ethanol to afford the title compound as tan crystals (0.17 g, 7.3%): mp 180° C.; MS (EI) m/z 314 (M+).

Example 16

8-(3-Chloro-phenyl-1,2,3,3a-tetrahydro-5H-pyrrolo [1,2-alquinoxalin-4-one

To a mixture of acetic acid (500 ml), 30% hydrogen peroxide (250 ml), and concentrated sulfuric acid (10 ml) was added 4-bromo-2-fluoroaniline (50 g, 0.26 mol) at 85±5° C. over 20 minutes. The reaction mixture was allowed to cool to room temperature and filtered. The solution was diluted with water and extracted with EtOAc (2×100 mL). The combined organic extracts were washed with water, then brine, dried (MgSO$_4$) and evaporated. The semisolid residue was filtered and the crude 4-bromo-2-fluoro-1-nitro-benzene was sublimed in vacuo to afford 4-bromo-2-fluoro-1-nitro-benzene (23 g, 40%): mp 82–83° C.; $^1$H-NMR (DMSO-d$_6$) δ 7.64–7.70 (m, 1H), 8.0 (dd, 1H, J=11.0, 1.98 Hz), 8.1 (t, 1H, J=8.57 Hz); MS (EI) m/z 219/221 (M+).

A mixture of 4-bromo-2-fluoro-1-nitro-benzene (9 g, 40 mmol), L-proline (4.6 g, 40 mmol), and potassium carbonate (7 g, 50 mmol) in ethanol (50 ml) and water (40 ml) was heated to reflux for 5 hours. After cooling to room temperature, the mixture was diluted with water and was adjusted to pH 6 with 1N aqueous HCl solution. The mixture was extracted with EtOAc (2×100 mL), the combined organic extracts were washed with water, then brine, dried (MgSO$_4$) and evaporated to afford N-(5-bromo-2-nitro-phenyl)-pyrrolidine-2-carboxylic acid (6 g, 48%) which was used in the next step without further purification.

A solution of N-(5-bromo-2-nitro-phenyl)-pyrrolidine-2-carboxylic acid (6 g, 23 mmol) and tin(II) chloride dihydrate (16.5 g, 73 mmol) in ethanol (200 ml), water (30 ml) and concentrated HCl (10 ml) was heated to reflux for 6 hours. After cooling to room temperature, the mixture was diluted with water and was adjusted to pH 9 with 2N aqueous sodium hydroxide solution. After addition of EtOAc, the precipitated tin hydroxide was filtered off The layers were separated and the organic layer was washed with water, then brine, dried (MgSO$_4$) and evaporated to afford 8-bromo-1,2,3,3a-tetrahydro-5H-pyrrolo[1,2-a]quinoxalin-4-one (3.7 g, 60%), which was used without further purification.

A solution of 8-bromo-1,2,3,3a-tetrahydro-5H-pyrrolo[1,2-a]quinoxalin-4-one (2.7 g, 10 mmol), 3-chlorophenyl boronic acid (1.6 g, 10 mmol), potassium carbonate (4 g, 30 mmol), and tetrakis(triphenylphosphine) palladium(0) (0.5 g, 0.43 mmol) in dimethoxyethane (100 ml), ethanol (25 ml), and water (25 ml) was heated to reflux for 6 hours. After cooling to room temperature, the mixture was diluted with water and extracted with EtOAc (3×60 mL). The combined organic extracts were washed with water, then brine, dried (MgSO$_4$) and evaporated. The crude product (1.5 g) was recrystallized from EtOAc/hexane to afford the title compound (0.2 g, 7%): mp 210° C.; MS (+APCI) m/z 299 ([M+H]$^+$).

Example 17

6-(3-Chloro-phenyl)-4-methyl-3,4-dihydro-1H-quinoxalin-4-one (5-Bromo-2-nitro-phenyl)-methyl-amino]-acetic acid A mixture of 4-bromo-2-fluoro-1-nitro-benzene (9 g, 40 mmol), sarcosine (3.6 g, 40 mmol), and potassium carbonate (5.5 g, 40 mmol) in ethanol (100 ml) and water (40 ml) was heated to reflux for 5 hours. After cooling to room temperature, the mixture was diluted with water and was adjusted to pH 6 with 1N aqueous HCl solution. The yellow precipitate was collected, washed with water and dried in vacuo to obtain crude [(5-bromo-2-nitro-phenyl)-methyl-amino]-acetic acid (10 g, 87%). A portion of the crude sample was recrystallized from EtOAc/hexane to afford the pure [(5-bromo-2-nitro-phenyl)-methyl-amino]-acetic acid: mp 152–155° C.; $^1$H-NMR (DMSO-d$_6$) δ 2.81 (s, 3H), 4.00 (s, 2H), 7.06 (dd, 1H, J=8.79, 1.98 Hz), 7.22 (d, 1H, J=1.98 Hz), 7.69 (d, 1H, J=8.79 Hz), 12.8 (s, 1H); MS (+APCI) m/z 289/291 (M+H)$^+$.

A solution of [(5-bromo-2-nitro-phenyl)-methyl-amino]-acetic acid (8 g, 27.6 mmol) and tin(II) chloride dihydrate (20 g, 88 mmol) in ethanol (200 ml), water (30 ml) and concentrated HCl (10 ml) was heated to reflux for 6 hours. After cooling to room temperature the mixture was diluted with water and was adjusted to pH 9 with 2N aqueous sodium hydroxide solution. After addition of EtOAc, the precipitated tin hydroxide was filtered off. The layers were separated and the organic layer was washed with water, then brine, dried (MgSO$_4$) and evaporated. The residue was recrystallized from ethanol to afford 6-bromo-4-methyl-3,4-dihydro-1H-quioxalin-2-one (2.4 g, 36%), which was used without further purification. $^1$H-NMR (DMSO-d$_6$) δ 2.78 (s, 3H), 3.89 (s, 2H), 6.81 (d, 1H, J=1.76 Hz), 6.95 (dd, 1H, J=8.49, 1.81 Hz), 7.05 (d, 1H, J=8.47 Hz), 10.63 (s, 1H).

A solution of 6-bromo-4-methyl-3,4-dihydro-1H-quioxalin-2-one (2.4 g, 10 mmol), 3-chlorophenyl boronic acid (1.6 g, 10 mmol), potassium carbonate (4 g, 30 mmol), and tetrakis(triphenylphosphine) palladium(0) (0.5 g, 0.43 mmol) in dimethoxyethane (100 ml), ethanol (25 ml), and water (25 ml) was heated to reflux for 6 hours. After cooling to room temperature, the mixture was diluted with water and extracted with EtOAc (3×50 mL). The combined organic extracts were washed with water, then brine, dried (MgSO$_4$) and evaporated. The residue was purified by column chromatography (SiO$_2$, EtOAc:hexane/1:6) to afford the title compound (0.58 g, 21%): mp 140° C.; $^1$H-NMR (DMSO-d$_6$) δ 2.82 (s, 3H), 3.65 (s, 2H), 6.82 (d, 1H, J=7.91 Hz), 6.90 (d, 1H, J=1.76 Hz), 6.99 (dd, 1H, J=8.13, 1.98 Hz), 7.3–7.32 (m, 1H), 7.39 (t, 1H, J=7.91 Hz), 7.55 (dt, 1H, J=7.91, 1.10 Hz), 7.64 (t, 1H, J=1.98 Hz), 10.47 (s, 1H); MS ((+)APCI) m/z 299 (M+H)$^+$.

Example 18

5-(3,4-Dihydro-4-methyl-2-oxo-quinaxalin-6-yl) thiophene-3-carbonitrile 3,4-Dihydro-4-methyl-2-oxo-quinoxalin-6-yl) boronic acid To a solution of 6-bromo-4-methyl-3,4-dihydro-1H-quinoxalin-2-one (3.6 g, 15 mmol) in THF (100 ml) was added sodium hydride (0.6 g, 15 mmol, 60% dispersion in mineral oil). After stirring 30 min. at room temperature, the mixture was cooled to –78° C. and butyl lithium (2.5M in hexanes, 6 ml, 15 mmol) was added slowly. After 30 min. triisopropyl borate (7rd, 30 mmol) was added and the mixture was allowed to warm to room temperature. After 2 hrs. hydrochloric acid (1N, 200 ml) and EtOAc (200 ml) were added. After stirring for 30 min., the pH was adjusted to 6 and the layers were separated. The aqueous phase was extracted with EtOAc, then the combined organic layers were washed with water, brine, dried (MgSO$_4$) and evaporated. The residue was triturated with ether, the precipitate was filtered off and dried in vacuo to obtain the subtitled compound (1.6 g, 52%) as an off-white solid: $^1$H-NMR (DMSO-d$_6$) δ 2.78 (s, 3H), 3.62 (s, 2H), 6.75 (d, J=7.58 Hz, 1H), 7.16 (s, 1H), 7.18 (d, J=7.86 Hz, 1H), 7.85 (s, 2H), 10.45 (s, 1H). MS (EI) m/z 207 (M+H)$^+$.

A mixture of 3,4-dihydro-4-methyl-2-oxo-quinoxalin-6-yl) boronic acid (1.6 g, 80 mmol), 2-bromo-4-cyanothiophene (1.5 g, 80 mmol), potassium carbonate (3.3 g, 24 mmol) and tetrakis(triphenylphosphine) palladium (0) (0.25 g, 0.2 mmol) in dimethoxyethane (70 ml), ethanol (15 ml), and water (15 ml) was heated to reflux for 6 hrs. After cooling to room temperature the mixture was diluted with water and extracted with EtOAc (3×40 mL). The combined organic layers were washed with water, then brine, dried (MgSO$_4$) and evaporated to obtain crude product (0.85 g, 40%). The residue was purified by column chromatography (SiO$_2$, 40% acetonitrile, 60% water) to afford the title compound: mp 270° C.; $^1$H-NMR (DMSO-d$_6$) δ 2.84 (s, 3H), 3.70 (s, 2H), 6.82 (d, J=7.91 Hz, 1H), 6.96 (d, J=1.76 Hz, 1H), 7.02 (dd, J=7.91, 1.76 Hz, 1H), 7.83 (d, J=1.32 Hz, 1H) 8.44 (d, J=1.32 Hz, 1H), 10.56 (s, 1H); MS (EI) m/z 269 (M$^+$).

Example 19

4-(n-Butyl)-6-(3-chloro-phenyl)-3,4-dihydro-1H-quinoxalin-2-one

[(5-Bromo-2-nitro-phenyl)-n-butyl-amino]acetic acid

A mixture of 4-bromo-2-fluoro-nitro benzene (34 g, 0.15 mol), N-n-butyl glycine (20 g, 0.15 mol) in ethanol (600 ml), and water (150 ml) was heated to reflux for 6 hours. After cooling to room temperature, the mixture was diluted with 2N sodium hydroxide, extracted with CH$_2$Cl$_2$ and the pH was adjusted to 5 with 1N HCl. The mixture was extracted with CH$_2$Cl$_2$, the CH$_2$Cl$_2$ solution was dried (MgSO$_4$) and evaporated to obtain the crude product (11 g, 22%) as a brown oil, which was used without further purification. $^1$H-NMR (DMSO-d$_6$) δ 0.84 (t, J=7.30 Hz, 3H), 1.23 (m, 2H), 1.45 (m, 2H), 3.18 (t, J=7.30 Hz, 2H), 3.91 (s, 2H), 7.16

(dd, J=8.68, 1.91 Hz, 1H), 7.40 (d, J=1.94 Hz, 1H), 7.69 (d, J=8.68 Hz, 1H); MS (EI) m/z 331 (M+).

6-Bromo-4-(n-butyl)-3,4-dihydro-1H-quinoxalin-2-one.

To a solution of [(5-bromo-2-nitro-phenyl)-n-butyl-amino]acetic acid (1 μg, 33 mmol) in acetic acid (150 ml) was added iron powder (6 g, 107 mmol) and the mixture was stirred for 2 hrs at 90° C. The reaction mixture was cooled and filtered and the acetic acid was evaporated. The remaining slurry was extracted with $CH_2Cl_2$ (3×50 mL). The combined $CH_2Cl_2$ extracts were combined, dried ($MgSO_4$) and evaporated (8.5 g, 90%). The product was used without further purification. $^1$H-NMR (DMSO-$d_6$) δ 0.93 (t, J=6.81 Hz, 3H), 1.35 (m, 2H), 1.51 (m, 2H), 3.18 (t, J=6.92 Hz, 2H), 3.75 (s, 2H), 6.6–6.9 (m, 3H), 10.50 (s, 1H).

A solution of 6-bromo-4-(n-butyl)-3,4-dihydro-1H-quinoxalin-2-one (8.5 g, 30 mmol), 3-chlorophenyl boronic acid (5 g, 30 mmol), potassium carbonate (12.5 g, 90 mmol) and tetrakis-(triphenylphosphine) palladium (0) (1.3 g, 1.1 mmol) in dimethoxyethane (200 ml), ethanol (50 ml), and water (50 ml) was heated to reflux for 6 hrs. After cooling to room temperature, the mixture was diluted with water and extracted with EtOAc (3×). The combined organic layers were washed with water, then brine, dried ($MgSO_4$) and evaporated to obtain crude product (7 g, 74%). The residue was purified by column chromatography ($SiO_2$, 20% EtOAc, 80% hexane) to afford the title compound, mp 110–115° C. $^1$H-NMR (DMSO-$d_6$) δ 0.93 (t, J=7.35 Hz, 3H), 1.36 (m, 2H), 1.56 (m, 2H), 3.30 (m, 2H), 3.74 (s, 2H), 6.84 (d, J=8.13 Hz, 1H), 6.90 (d, J=1.54 Hz, 1H), 6.95 (dd, J=8.13, 1.54 Hz, 1H) 7.35 (n, 1H), 7.43 (t, J=7.91 Hz, 1H), 7.55 (n, 1H), 7.63 (t, J=1.76 Hz, 1H), 10.50 (s, 1 Hz). MS ([+] APCI) m/z 315 [M+H]$^+$+1 chlorine.

Example 20

6(3-Cyano-5-fluorophenyl)-4-isopropyl-3,4-dihydro-1H-quinoxalin-2-one

[(5-Bromo-2-nitro-phenyl)-isopropyl-amino]-acetic acid

A mixture of 4-bromo-2-fluoro-1-nitrobenzene (52 g, 0.24 mol), n-isopropylglycine (26 g, 0.22 mol), potassium carbonate (32 g, 0.23 mol) in ethanol (700 ml) and water (140 ml) was heated to reflux for 3 hrs. After cooling to room temperature the mixture was diluted with water, extracted with $CHCl_3$, and the pH was adjusted to 5 with 1N HCl. The yellow precipitate was filtered off, washed with water and dried in vacuo (31 g, 44%): $^1$H-NMR (DMSO-$d_6$) δ 1.08 (d, J=6.50 Hz, 6H), 3.55 (septet, J=6.50 Hz, 1H), 3.92 (s, 2H), 7.25 (dd, J=8.65, 1.72 Hz, 1H), 7.53 (d, J=1.69 Hz, 1H), 7.69 (d, J=8.65 Hz, 1H), 12.52 (bs, 1H).

6-Bromo-4-isopropyl-3,4-dihydro-1H-quinoxalin-2-one

To a solution of [(5-bromo-2-nitro-phenyl)-isopropyl-amino]acetic acid (27 g, 85 mmol) in acetic acid (400 ml) was added iron powder (15 g, 0.27 mol) and the mixture was stirred for 2 hrs. at 90° C. The reaction mixture was cooled, filtered, and the acetic acid was evaporated. The remaining slurry was extracted with $CH_2Cl_2$ (3×300 ml). The $CH_2Cl_2$ extracts were combined, dried ($MgSO_4$) and evaporated to afford the subtitled compound (16.8 g, 73%): $^1$H-NMR (DMSO-$d_6$) δ 1.13 (d, J=6.54 Hz, 6H), 3.57 (s, 2H), 3.99 (septet, J=6.54 Hz, 1H), 6.82 (dd, J=8.23, 1.88 Hz, 1H), 6.72 (d, J=8.17 Hz, 1H), 6.90 (d, J=1.59 Hz, 1H), 10.50 (s, 1H): MS (EI) 267/269 (M)$^+$+1 bromine.

(4-Isopropyl-2-oxo-3,4-dihydro-quinoxalin-6-yl)boronic acid

To a solution of 6-bromo-4-isopropyl-3,4-dihydro-1H-quinoxalin-2-one (8.1 g, 30 mmol) in THF (200 ml) was added sodium hydride (60% dispersion in mineral oil, 1.2 g, 30 mmol). After stirring for 30 min. at room temperature, the mixture was cooled to −78° C. and butyl lithium (2.5 M in hexanes, 12.5 ml, 30 mmol) was added slowly. After 30 min. triisopropyl borate (19 ml, 83 mmol) was added and the mixture was allowed to warm to room temperature. After 2 hours, hydrochloric acid (1N, 350 ml) and ethyl acetate (350 ml) were added. After stirring for 30 min., the pH was adjusted to 6 and the layers were separated. The aqueous phase was extracted with ethyl acetate, the combined organic layers were washed with water, brine, dried ($MgSO_4$) and evaporated. The residue was triturated with ether, the precipitate filtered off and dried in vacuo to obtain the subtitled compound (3.5 g, 50%) as an off-white solid that was used without further purification. $^1$H-NMR (DMSO-$d_6$) δ 1.15 (d, J=6.56 Hz, 6H), 3.51 (s, 2H), 4.04 (septet, J=6.57 Hz, 1H), 6.76 (d, J=7.65 Hz, 1H), 7.14 (d, J=7.66 Hz, 1H), 7.27 (s, 1H), 7.84 (s, 2H), 10.41 (s, 1H).

A solution of (3,4-dihydro-4-isopropyl-2-oxoquinoxalin-6-yl)boronic acid (1.15 g, 4.9 mmol), 3-bromo-5-fluoro-benzonitrile (1.08 g, 5.4 mmol), potassium carbonate (2.75 g, 22 mmol), and tetrakis(triphenylphosphine)palladium(0) (0.25 g, 0.2 mmol) in dimethoxyethane (70 ml), ethanol (15 ml) and water (15 mol) was heated to reflux for 6 hrs. After cooling to room temperature the mixture was concentrated and the residue was dissolved in ethyl acetate and 2N sodium hydroxide. The organic layer was washed with water, then brine, dried ($MgSO_4$) and evaporated. The residue was triturated with ether, and the precipitate was filtered off to afford the title compound, mp 238–240° C. (0.5 g, 30%); $^1$H-NMR (DMSO-$d_6$) δ 1.17 (d, J=6.49 Hz, 6H), 3.59 (s, 1H), 4.30 (septet, J=6.54 Hz, 1H), 6.89 (d, J=8.00 Hz, 1H), 7.11 (d, J=8.08 Hz, 1H), 7.76 (d, J=8.34 Hz, 1H), 7.91 (d, J=10.47 Hz, 1H), 8.06 (s, 1H), 10.56 (s, 1H). MS (ESI) m/z 308 [M–H]$^{-1}$.

Example 21

6-(3-Chloro-4-fluoro-phenyl)-4-isopropyl-3,4-dihydro-1H-quinoxalin-2-one

A mixture of (3,4-dihydro-4-isopropyl-2-oxoquinoxalin-6-yl)boronic acid (2.4 g, 10 mmol), 4-bromo-2-chlorofluorobenzene (2 g, 10 mmol), potassium carbonate (4 g, 30 mmol), and tetrakis(triphenylphosphine)palladium(0) (0.46 g, 0.4 mmol) in dimethoxyethane (100 ml), ethanol (25 ml) and water (25 mol) was heated to reflux for 6 hrs. After cooling to room temperature the mixture was diluted with water and extracted with ethyl acetate (3×). The combined organic layers were washed with water, then brine, dried ($MgSO_4$) and evaporated to obtain crude product (2.9 g, 91%). Recrystallization from EtOAc/hexane afforded the title compound, mp 208–213° C.: $^1$H-NMR (DMSO-$d_6$) δ 1.16 (d, J=6.59 Hz, 6H), 3.56 (s, 2H), 4.22 (septet, J=6.59 Hz, 1H), 6.86 (d, J=7.91 Hz, 1H), 6.96 (dd, J=7.91, 1.76 Hz, 1H), 7.01 (d, J=1.76 Hz, 1H), 7.43 (t, J=9.01 Hz, 1H), 7.61 (m, H), 7.82 (dd, J=7.14, 2.31 Hz, 1H), 10.47 (s, 1H). MS (EI) m/z 318 [M]$^+$+1 chlorine.

Example 22

6-(3-Chloro-phenyl)-4-isopropyl-3,4-dihydro-1H-quinoxalin-2-one

A mixture of 6-bromo-4-isopropyl-3,4-dihydro-1H-quinoxalin-2-one (2 g, 75 mmol), 3-chlorophenylboronic acid (1.6 g, 10 mmol), potassium carbonate (4 g, 30 mmol) and tetrakis(triphenylphosphine)palladium(0) (0.4 g, 0.35 mmol) in dimethoxyethane (100 ml), ethanol (25 ml), and water (25 ml) was heated to reflux for 6 hrs. After cooling to room temperature the mixture was diluted with water and extracted with EtOAc (3×50 mL). The combined organic layers were washed with water, then brine, dried (MgSO$_4$) and evaporated to give crude product (1.5 g, 66%). Recrystallization from EtOAc/hexane afforded the title compound: mp 146–150° C. $^1$H-NMR (DMSO-d$_6$) δ 1.16 (d, J=6.37 Hz, 6H), 3.57 (s, 2H), 4.21 (septet, J=6.59 Hz, 1H), 6.87 (d, J=7.91 Hz, 1H), 6.98 (dd, J=7.91, 1.76 Hz, 1H), 7.02 (d, J=1.76 Hz, 1H), 7.35 (m, 1H), 7.43 (t, J=7.69 Hz, 1H), 7.57 (m, 1H), 7.66 (t, J=1.76 Hz, 1H), 10.48 (s, 1H). MS (EI) m/z 300 (M)$^+$+1 chlorine.

Example 23

Pharmacology

The compounds of this invention were tested in the relevant assay as described below and their potency are in the range of 0.01 mM to 5 mM in the in vitro assays and 0.001 to 300 mg/kg in the in vivo assays. The selected examples are listed in Table 1 and 2.

TABLE 1

| Compound | R$_1$ | R$_2$ | R$_3$ | Alkaline Phosphatase IC$_{50}$ (nM) | hPR CV-1 IC$_{50}$ (nM) |
|---|---|---|---|---|---|
| 1 | 3-chlorophenyl | Bn | H | | 412 |
| 2 | 3-nitrophenyl | Bn | H | | 230 |
| 3 | 3-chlorophenyl phenyl | Me | H | | 1370 |
| 4 | 3-nitrophenyl | Me | H | | 1529 |
| 5 | 3-nitrophenyl | H | Me | | 750 |
| 6 | 3-nitrophenyl | isopropyl | H | | 147 |
| 7 | 3-chlorophenyl | isopropyl | H | | 155 |

TABLE 2

| Compound | R$_1$ | R$_2$ | Alkaline Phosphatase IC$_{50}$ (nM) | hPR CV-1 IC$_{50}$ (nM) |
|---|---|---|---|---|
| B1 | 3-nitrophenyl | H | | 220 |
| B2 | 3-nitrophenyl | Et | | 295 |
| C1 | 3-chlorophenyl | Me | 600 | 1585 |
| C2 | 3-chlorophenyl | H | 550 | 525 |
| C3 | 2-(4-cyanothiophenyl) | Me | 300 | |
| C4 | 3-chlorophenyl | isopropyl | 850 | |
| C5 | 3-chloro-4-fluoro-phenyl | isopropyl | 700 | |
| C6 | 3-chlorophenyl | n-Bu | 500 | |

1. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium

DMEM:F12 (1:1)

(GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium

Minimum Essential

Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture

Stock T47 D cells are maintained in growth medium. For BrdU incorporation assay, cells are plated in 96-well plates (Falcon, Becton Dickinson Labware) at 10,000 cells/well in growth medium After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 μl of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear dose response analyses in both single dose and dose response studies.

f. Reference Compounds

Trimegestone and medroxyprogesterone acetate (MPA) are reference progestins and RU486 is the reference antiprogestin. All reference compounds are run in full dose-response curves and the EC$_{50}$ or IC$_{50}$ values are calculated.

TABLE 3

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
| | 2 | 0.014 | 0.001 | 0.011 | 0.017 |
| | 3 | 0.019 | 0.001 | 0.016 | 0.024 |
| MPA | 1 | 0.019 | 0.001 | 0.013 | 0.027 |
| | 2 | 0.017 | 0.001 | 0.011 | 0.024 |

TABLE 4

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
| | 2 | 0.016 | 0.001 | 0.014 | 0.020 |
| | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE 2. Rat Decidualization Assay The objective of this procedure is used to evaluate the effect of progestins and antiprogestins on rat uterine decidualization and compare the relative potencies of various test compounds. The materials and methods used in this assay are as follows.

a. Methods

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC protocol #5002)

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg . . . ).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds

All progestin reference compounds were run in full dose-response curves and the $EC_{50}$ for uterine wet weight were calculated.

TABLE 5

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
| | 2 | 6.21 | 1.12 | 4.41 | 8.76 |
| 3-Ketodesogestrel | 1 | 0.11 | 0.02 | 0.07 | 0.16 |
| | 2 | 0.10 | 0.05 | 0.11 | 0.25 |
| | 3 | 0.06 | 0.03 | 0.03 | 0.14 |
| Levonorgestrel | 1 | 0.08 | 0.03 | 0.04 | 0.16 |
| | 2 | 0.12 | 0.02 | 0.09 | 0.17 |
| | 3 | 0.09 | 0.02 | 0.06 | 0.13 |
| | 4 | 0.09 | 0.02 | 0.06 | 0.14 |
| MPA | 1 | 0.42 | 0.03 | 0.29 | 0.60 |
| | 2 | 0.39 | 0.05 | 0.22 | 0.67 |
| | 3 | 0.39 | 0.04 | 0.25 | 0.61 |

TABLE 6

Estimated average $EC_{50}$, standard error, and 95% confidence intervals for dose-response curves of 3 reference compounds

| Compound | EC50 (mg/kg, s.c.) | SE | 95% CI. lower | 95% CI. upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 7

Estimated $IC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
| | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: $[(D-C)/C] \times 100\%$

Progestational activity: Compounds that induce decidualization significantly ($p<0.05$) compared to vehicle control are considered active Antiprogestational activity: Compounds that decrease $EC_{50}$ progesterone induced decidualization significantly ($p<0.05$)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

3. PRE-luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Growth Medium

DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). Experimental medium: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase Assay

Stock CV-1 cells are maintained in growth medium Co-transfection is done using $1.2 \times 10^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium Cells are then treated with reference or test compounds in experimental medium Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in full dose response curves and the $EC_{50}$ or $IC_{50}$ values are calculated.

TABLE 8

Estimated $EC_{50}$, standard error (SE), and 95% confidence intervals (CI) for reference progestins from three individual studies

| Compound | Exp. | $EC_{50}$ (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 9

Estimated $IC_{50}$, standard error (SE), and 95% confident interval (CI) for the antiprogestin, RU486 from three individual studies

| Compound | Exp. | $IC_{50}$ (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly ($p<0.05$) compared to vehicle control are considered active.

Antiprogestational activity: Compounds that decrease 3 nM progesterone induced PRE-luciferase activity significantly ($p<0.05$)

$EC_{50}$: Concentration of a compound that gives half-maximal increase PRE luciferase activity (default-nM) with SE.

$IC_{50}$: Concentration of a compound that gives half-maximal decrease in 3 nM progesterone induced PRE-luciferase activity (default-nM) with SE.

4. T47D Cell Alkaline Phosphatase Assay

The purpose of this assay is to identify progestins or antiprogestins by determining a compound's effect on alkaline phosphatase activity in T47D cells. The materials and methods used in this assay are as follows.

a. Culture Medium

DMEM:F12 (1:1) (GIBCO, BRL) supplemented with 5% (v/v) charcoal stripped fetal bovine serum (not heat-inactivated), 100 U/ml penicillin, 100 μg/n streptomycin, and 2 mM GlutaMax (GIBCO, BRL).

b. Alkaline Phosphatase Assay Buffer

I. 0.1 M Tris-HCl, pH 9.8, containing 0.2% Triton X-100

II. 0.1 M Tris-HCl, pH 9.8 containing 4 mM p-nitrophenyl phosphate (Sigma).

c. Cell Culture and Treatment

Frozen T47D cells were thawed in a 37° C. water bath and diluted to 280,000 cells/ml in culture medium. To each well in a 96-well plate (Falcon, Becton Dickinson Labware), 180 μl of diluted cell suspension was added. Twenty μl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay

At the end of treatment, the medium was removed from the plate and fifty μl of assay buffer I was added to each well. The plates were shaken in a titer plate shaker for 15 min. Then 150 μl of assay buffer II was added to each well. Optical density measurements were taken at 5 min intervals for 30 min at a test wavelength of 405 nM.

e. Analysis of Results

Analysis of dose-response Data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Progesterone and trimegestone are reference progestins and RU486 is the reference antiprogestin. All reference compounds are run in full dose response curves and the $EC_{50}$ or $IC_{50}$ values are calculated.

TABLE 10

Estimated $EC_{50}$, standard error (SE), and 95% confidence intervals (CI) for reference progestins from three independent experiments

| Compound | Exp. | $EC_{50}$ (nM) | SE | 95% CI lower | 95% CI upper |
|---|---|---|---|---|---|
| Progesterone | 1 | 0.839 | 0.030 | 0.706 | 0.996 |
|  | 2 | 0.639 | 0.006 | 0.611 | 0.669 |
|  | 3 | 1.286 | 0.029 | 1.158 | 1.429 |
| Trimegestone | 1 | 0.084 | 0.002 | 0.076 | 0.091 |
|  | 2 | 0.076 | 0.001 | 0.072 | 0.080 |
|  | 3 | 0.160 | 0.004 | 0.141 | 0.181 |

TABLE 11

Estimated $IC_{50}$, standard error, and 95% confident interval for the reference antiprogestin RU486 from three independent experiments

| Compound | Exp | $IC_{50}$ (nM) | SE | 95% CI lower | 95% CI upper |
|---|---|---|---|---|---|
| RU486 | 1 | 0.103 | 0.002 | 0.092 | 0.115 |
|  | 2 | 0.120 | 0.001 | 0.115 | 0.126 |
|  | 3 | 0.094 | 0.007 | 0.066 | 0.134 |

Example 24

1-Benzyl-6-(3-chlorophenyl)-1,3-dihydro-2H-benzimidazole-2-thione

To a solution of 1-benzyl-6-(3-chlorophenyl)-1,3-dihydro-2H-benzimidazole-2-one (0.1 g, 0.3 mmol) in anhydrous toluene was added under a blanket of nitrogen Lawesson's reagent (0.133 g, 0.33 mmol). The mixture was heated to 110° C. under nitrogen for 3 hours, allowed to cool to ambient temperature, and the solvent was removed. The residue was purified by a silica gel chromatography (hexane:ethyl acetate/5:1) to give the title compound as a yellow solid (0.03 g, 29%): mp 211–212° C.; $^1$H-NMR (DMSO-$d_6$) δ 12.99 (s, 1H), 7.70 (t, 1H, J=1.7 Hz), 7.64 (m, 1H), 7.58–7.61 (m, 1H), 7.25–7.54 (m, 9H), 5.59 (s, 2H); MS (ESI) m/z 349 [M–H]$^-$; Anal. Calc. For $C_{20}H_{15}ClN_2S$: C, 68.46, H, 4.31, N, 7.98. Found: C, 68.07, H, 4.23, N, 7.88.

Example 25

1-Benzyl-6-(3-nitrophenyl)-13-dihydro-2H-benzimidazole-2-thione

Prepared according to the procedure for Example 24 from 1-benzyl-6-(3-nitrophenyl)-1,3-dihydro-2H-benzimidazole-2-one (0.1 g, 0.29 mmol) and Lawesson's reagent (0.13 g, 0.32 mmol). A yellow solid (0.025 g, 24%): mp 244–245° C.; $^1$H-NMR (DMSO-d,) δ 13.08 (s, 1H), 8.43 (s, 1H), 8.20 (dd, 1H, J=8.2, 1.7 Hz), 8.12 (d, 1H, J=7.8 Hz), 7.72–7.78 (in, 2H), 7.62 (d, 1H, J=8.3 Hz), 7.25–7.43 (m, 6H), 5.62 (s, 2H); MS (ESI) m/z 360 [M–H]$^-$; Anal. Calc. For $C_{20}H_{15}ClN_2S.0.2H_2O$: C, 65.81, H, 4.25, N, 11.51. Found: C, 65.56, H, 4.11, N, 11.29.

Example 26

6-(3-Nitro-phenyl)4-methyl-3,4-dihydro-1H-quinoxalin-2-one

Prepared according to the procedure for Example 5 from 6-bromo-4-methyl-3,4-dihydro-1H-quinoxalin-2-one (4.8 g, 20 mmol), and 3-nitrophenylboronic acid (4.8 g, 30 mmol). A red powder (0.95 g, 16%): mp 237–243° C. $^1$H-NMR (DMSO-$d_6$) δ 2.88 (s, 3H), 6.9 (d, J=7.9 Hz, 1H), 7.01 (d, J=2 Hz, 1H), 7.11 (dd, J=7.9, 2.0 Hz, 1H), 7.7 (t, J=7.9 Hz, 1H), 8.1 (m, 2H), 8.37 (t, J=0.7 Hz), MS (ESI) m/z 283(M)$^+$.

Example 27

6-(4-Chloro-phenyl)-3-methyl-3,4-dihydro-1H-quinoxalin-2-one

A mixture of 4-bromo-2-fluoro-1-nitro-benzene (22 g, 100 mmol), L-alanine (8.9 g, 100 mmol), and potassium carbonate (17.5 g, 125 mmol) in ethanol (250 ml), and water (200 ml) was heated to reflux for 5 hours. After cooling to room temperature, the mixture was diluted with water, and acidified with 1N hydrochloric acid. The precipitate was collected on a funnel and dried to afford N-(5-bromo-2-nitrophenyl)-alanine (28.9 g, 100%). A sample was recrystallized from ethanol: m.p. 183–187° C.; $^1$H-NMR (DMSO-$d_6$) δ 1.44 (d, J=6.9 Hz, 3H), 4.56 (m, 1H), 6.87 (d, J=6 Hz, 1H), 7.21 (d, J=1.7 Hz, 1H), 7.99 (d, J=7 Hz, 1H), 8.36 (d, J=7 Hz, 1H), 13.27 (s, 1H).

To a solution of N-(5-bromo-2-nitrophenyl)-alanine (22 g, 76 mmol) in acetic acid (300 ml) was added iron powder (10 g, 180 mmol), and the mixture was stirred for 2 hours at 90° C. The reaction mixture was cooled and filtered, and the acetic acid was evaporated. The remaining slurry was extracted with methylene chloride (3×200 ml). The combined extracts were combined, dried over magnesium sulfate, filtered, and evaporated to afford 6-bromo-3-methyl-3,4-dihydro-1H-quinoxalin-2-one (9.4 g, 51%). A sample was recrystallized from ethanol: m.p. 133–135° C. $^1$H-NMR (DMSO-$d_6$) δ 1.23 (d, J=6.81 Hz, 3H), 3.80 (q, J=6.81 Hz, 1H), 6.27 (bs, 1H), 6.63 (d, J=8.35 Hz, 1H), 6.72 (dd, J=8.35, 1.76 Hz, 1H), 6.80 (d, J=1.76 Hz, 1H), 10.29 (s, 1H).

A solution of 6-bromo-3-methyl-3,4-dihydro-(H-quinoxalin-2-one 2.4 g, 10 mmol), 4-chlorophenyl boronic acid (1.6 g, 10 mmol), potassium carbonate (4 g, 30 mmol), and tetrakis-(triphenylphosphine)palladium (0) in dimethoxyethane (150 ml ), ethanol (25 ml), and water (25 ml) was heated to reflux for 6 hours. After cooling to room temperature the mixture was diluted with water, and extracted with ethyl acetate. The organic layer was separated, dried over magnesium sulfate, filtered, and concentrated to obtain crude product (0.83 g, 30%). A sample was recrystallized from ethanol to afford the title compound: m.p. 228–230° C. $^1$H-NMR (DMSO-d$_6$) δ 1.28 (d, J=6.63 Hz, 3H), 3.83 (q, J=6.63 Hz, 1H), 6.16 (bs, 1H), 6.81 (d, J=8.00 Hz, 1H), 6.91 (dd, J=8.05, 1.9 Hz, 1H), 6.95 (d, J=1.7 Hz, 1H), 7.46 (d, J=8.6 Hz, 2H), 7.55 (d, J=8.6 Hz, 2H), 10.32 (s, 1H); MS (EI) m/z 272/274.

Example 28

4-Benzyl-6-(3-chlorophenyl)-3,4-dihydroquinoxalin-2 (1H)-one

In a manner as described above, 4-bromo-2-fluoro-1-nitro-benzene (11 g, 50 mmol), and N-benzyl-glycine ethyl ester (10 g, 50 mmol) were reacted to give crude [(5-bromo-nitro-phenyl)-benzyl-amino]-acetic acid (10 g, 55%). This product was reacted with iron powder to obtain crude 4-benzyl-6-bromo-3,4-dihydroquinoxalin-2(1H)-one (5 g, 58%). A sample was recrystallized from ethyl acetate/hexane: m.p.174–176° C. $^1$H-NMR (DMSO-d,) δ 3.75 (s, 2H), 4.43 (s, 2H), 6.71 (d, J=1.9 Hz, 1H), 6.81 (m, 2H), 7.32 (m, 5H), 10.57 (s, 1H).

The title compound was prepared according to the procedure for Example 5 from 4-benzyl-6-bromo-3,4-dihydroquinoxalin-2(1H)-one (1.6 g, 5 mmol), and 3-chlorophenyl boronic acid (0.8 g, 5 mmol). An off-white powder (0.9 g, 51%): m.p.182–185° C. $^1$H-NMR (DMSO-d$_6$) δ 3.74 (s, 2H), 4.54 (s, 2H), 6.87 (d, J=0.7 Hz), 7.0 (m, 2H), 7.36 (m, 8H), 7.52 (t, J=1.8 Hz, 1H), 10.57 (s, 1H), MS (ESI) m/z 349 (M+H)$^+$.

Example 29

Isopropyl 7-(3-chlorophenyl)-3-oxo-3,4-dihydroquinoxalin-1(2H)-carboxylate

To a solution of 7-bromo-3-oxo-3,4-dihydroquinoxaline (6.8 g, 30 mmol) in pyridine (50 ml) was added a solution of isopropyl chloroformate in toluene (35 ml, 1M, 35 mmol) over 30 minutes. The mixture was triturated with water/chloroform, the organic layer was separated, washed with brine, dried over magnesium sulfate, and evaporated to obtain crude isopropyl 7-bromo-3-oxo-3,4-dihydroquinoxaline-1(2H)-carboxylate(9.3 g, 97%). A sample was recrystallized from ethanol: m.p. 159–161° C. $^1$H-NMR (DMSO-d$_6$) δ 1.25 (d, J=6.2 Hz, 6H), 4.25 (s, 2H), 4.90 (Sep, J=6.2 Hz, 1H), 6.89 (d, J=8.6 Hz, 1H), 7.27 (dd, J=9.1, 2.1 Hz, 1H), 7.74 (s, 1H), 12.51 (s, 1H), MS (ESI) m/z 330/332 (M+NH$_4$)$^+$.

The title compound was prepared according to the procedure for Example 5 from isopropyl 7-bromo-3-oxo-3,4-dihydroquinoxaline-1 (2H)-carboxylate (6.3 g, 20 mmol), and 3-chlorophenyl boronic acid (3.2 g, 20 mmol). Off-white crystals (3.7 g, 49%): m.p. 174–176° C. $^1$H-NMR (DMSO-d$_6$) δ 1.27 (d, J=6.4 Hz, 6H), 4.30 (s, 2H), 4.94 (sep, J=6.2 Hz, 1H), 7.04 (d, J=8.3 Hz, 1H), 7.50 (m, 4H), 7.61 (t, J=1.9 Hz, 1H), 7.86 (s, 1H), 10.79 (s, 1H), MS(APCI) m/z 345/347 (M+H)$^+$.

Example 30

Isopropyl 7-(3-chlorophenyl)-3-thioxo-3,4-dihydroquinoxaline-1(2H)-carboxylate

Prepared according to the procedure for Example 24 from isopropyl 7-(3-chlorophenyl)-3-oxo-3,4-dihydroquinoxaline-1(2H)-carboxylate and Lawesson's reagent. A yellowish solid: m.p. 208–212° C.; $^1$H-NMR (DMSO-d$_6$) δ 1.27 (d, J=6.1 Hz, 6H), 4.62 (s, 2H), 4.94 (sep, J=6.1 Hz, 1H), 7.23 (m, 4H), 7.64 (t, J=1.8 Hz, 1H), 7.90 (s, 1H), 12.80 (s, 1H), MS (ESI) m/z 359/361 (M–H)-.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:

1. A method of contraception, which comprises administering to a female of child bearing age over a period of 28 consecutive days:
   a) a first phase of from 18 to 21 daily dosage units of a progestational agent equal in progestational activity to about 35 to about 150 μg levonorgestrel, and ethinyl estradiol at a daily dose range of from about 10 to about 35 μg;
   b) a second phase of from 1 to 7 daily dosage units of a daily dose of from about 2 to 50 mg of an antiprogestin of the formula:

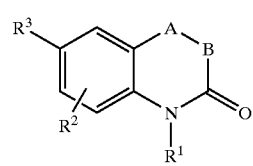

wherein:

A is O, S, or NR$^4$;

B is a bond between A and C=O, or the moiety CR$^5$R$^6$;

R$^4$, R$^5$, and R$^6$ are independently selected from the group consisting of H, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$cycloalkyl, aryl, substituted aryl, heterocyclic, and substituted heterocyclic;

or R$^4$ and R$^5$ are fused to form a 5 to 7 membered ring;

R$^1$ is selected from the group consisting of H, OH, NH$_2$, C$_1$ to C$_6$ alkyl, substituted C$_1$ to C$_6$ alkyl, C$_3$ to C$_6$ alkenyl, substituted C$_3$ to C$_6$ alkenyl, alkynyl, substituted alkynyl, and COR$^A$;

R$^A$ is selected from the group consisting of H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, and substituted C$_1$ to C$_3$ aminoalkyl;

R$^2$ is selected from the group consisting of H, halogen, CN, NO$_2$, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, and substituted C$_1$ to C$_6$ aminoalkyl;

R$^3$ is selected from the group consisting of (i) and (ii):
   (i) a substituted benzene ring having the substituents X, Y and Z and of the formula:

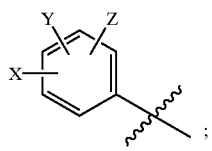

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^B$, $OCOR^B$, and $NR^C COR^B$;

$R^B$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^C$ is H, $C_1$ to $C_3$ alkyl, or substituted $C_1$ to $C_3$ alkyl;

Y and Z are independent substituents selected from the group consisting of H, halogen, CN, $NO_2$, $C_1$ to $C_3$ alkoxy, $C_1$ to $C_3$ alkyl, and $C_1$ to $C_3$ thioalkoxy; and (ii) a five or six membered ring having it its backbone 1, 2, or 3 heteroatoms selected from the group consisting of O, S, SO, $SO_2$ and $NR^7$ and having one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^D$, and $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

$R^7$ is H or C to $C_3$ alkyl;

or a pharmaceutically acceptable salt thereof, and c) optionally, an orally and pharmaceutically acceptable placebo for each remaining day of the 28 consecutive days.

2. The method according to claim 1, wherein the progestational agent is levonorgestrel and wherein:

$R^1$ is H, OH, $NH_2$, $C_1$ to $C_6$ alkyl, substituted $C_1$ to $C_6$ alkyl, or $COR^A$;

$R^A$ is H, $C_1$ to $C_3$ alkyl, or $C_1$ to $C_3$ alkoxy;

$R^2$ is H, halogen, $NO_2$, $C_1$ to $C_3$ alkyl, or substituted $C_1$ to $C_3$ alkyl;

$R^3$ is the substituted benzene ring having the substituents X and Y and of the structure:

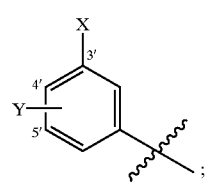

wherein:

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkoxy;

Y is on the 4' or 5' position and is selected from the group consisting of H, halogen, CN, $NO_2$, $C_1$ to $C_3$ alkoxy, $C_1$ to $C_3$ alkyl, and $C_1$ to $C_3$ thioalkoxy.

3. The method according to claim 1, wherein the progestational agent is levonorgestrel and wherein:

$R^3$ is the five membered ring of the structure:

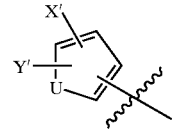

wherein:

U is O, S, or $NR^7$;

X' is selected from the group consisting of halogen, CN, $NO_2$, $C_1$ to $C_3$ alkyl and $C_1$ to $C_3$ alkoxy;

Y' is H or $C_1$ to $C_3$ alkyl.

4. The method according to claim 1, wherein the progestational agent is levonorgestrel and wherein:

$R^3$ is the six membered ring of the structure:

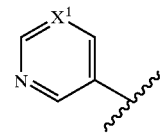

wherein:

$X^1$ is N or $CX^2$;

$X^2$ is halogen, CN or $NO_2$.

5. The method according to claim 1, wherein the progestational agent is levonorgestrel and the antiprogestin compound has the structure:

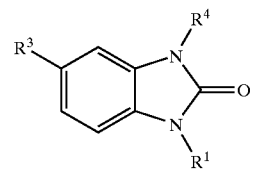

wherein:

$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^4$ is H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, or substituted aryl, wherein said aryl is benzyl; and $R^3$ is the substituted benzene ring having the structure:

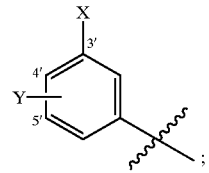

wherein:

X is selected from the group consisting of halogen, CN, $C_1$ to $C_3$ alkoxy, $C_1$ to $C_3$ alkyl, $NO_2$, $C_1$ to $C_3$ perfluoroalkyl, and $C_1$ to $C_3$ thioalkoxy;

Y is on the 4' or 5' position and is selected from the group consisting of H, halogen, CN, $NO_2$, $C_1$ to $C_3$ alkoxy, $C_1$ to $C_3$ alkyl, and $C_1$ to $C_3$ thioalkoxy.

6. The method according to claim 1 wherein the antiprogestin is 1-Benzyl-6-(3-chloro-phenyl)-1,3-dihydro-benzoimidazol-2-one or a pharmaceutically acceptable salt thereof.

7. The method according to claim 1 wherein the antiprogestin is 1-Benzyl-6-(3-nitro-phenyl)-1,3-dihydro-benzoimidazol-2-one or a pharmaceutically acceptable salt thereof.

8. The method according to claim 1, wherein the antiprogestin is 1-Methyl-6-(3-nitro-phenyl)-1,3-dihydro-benzoimidazol-2-one or a pharmaceutically acceptable salt thereof.

9. The method according to claim 1 wherein the antiprogestin is 6-(3-chloro-phenyl)-1-methyl-1,3-dihydro-benzoimidazol-2-one or a pharmaceutically acceptable salt thereof.

10. The method according to claim 1 wherein the antiprogestin is 5-(3-Nitro-phenyl)-1,3-dihydro-benzoimidazol-2-one or a pharmaceutically acceptable salt thereof.

11. The method according to claim 1 wherein the antiprogestin is 6-(3-Nitro-phenyl)-3H-benzooxazol-2-one or a pharmaceutically acceptable salt thereof.

12. The method according to claim 1 wherein the antiprogestin is 6-(3-Nitro-phenyl)-3H-benzothiazol-2-one or a pharmaceutically acceptable salt thereof.

13. The method according to claim 1 wherein the antiprogestin is 6-(3-Chloro-phenyl)-3H-benzothiazol-2-one or a pharmaceutically acceptable salt thereof.

14. The method according to claim 1 wherein the antiprogestin is 7-(3-Nitro-phenyl)-4H-benzo[1,4]thiazin-3-one or a pharmaceutically acceptable salt thereof.

15. The method according to claim 1 wherein the antiprogestin is 2-Ethyl-7-(3-nitro-phenyl)-4H-benzo[1,4]thiazin-3-one or a pharmaceutically acceptable salt thereof.

16. The method according to claim 1 wherein the antiprogestin is 8-(3-Chloro-phenyl-1,2,3,3a-tetrahydro-5H-pyrrolo[1,2-a]quinoxalin-4-one or a pharmaceutically acceptable salt thereof.

17. The method according to claim 1 wherein the antiprogestin is 6-(3-Chloro-phenyl)-4-methyl-3,4-dihydro-1H-quinoxalin-4-one or a pharmaceutically acceptable salt thereof.

18. The method according to claim 1 wherein the antiprogestin is 5-(3,4-Dihydro-4-methyl-2-oxo-quinoxalin-6-yl) thiophene-3-carbonitrile or a pharmaceutically acceptable salt thereof.

19. The method according to claim 1 wherein the antiprogestin is 4-(n-Butyl)-6-(3-chloro-phenyl)-3,4-dihydro-1H quinoxalin-2-one or a pharmaceutically acceptable salt thereof.

20. The method according to claim 1 wherein the antiprogestin is 6-(3-Cyano-5-fluorophenyl)-4-isopropyl-3,4-dihydro-1H-quinoxalin-2-one or a pharmaceutically acceptable salt thereof.

21. The method according to claim 1 wherein the antiprogestin is 6-(3-Chloro-4-fluoro-phenyl)-4-isopropyl-3,4-dihydro-1H-quinoxalin-2-one or a pharmaceutically acceptable salt thereof.

22. The method according to claim 1 wherein the antiprogestin is 6-(3-Chloro-phenyl)-4-isopropyl-3,4-dihydro-1H-quinoxalin-2-one or a pharmaceutically acceptable salt thereof.

23. The method according to claim 1 wherein the progestational agent is selected from the group consisting of levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl) norgestimate.

24. The method of contraception according to claim 1, which comprises administering to a female of child bearing age over a period of 28 consecutive days:

a) a first phase of 21 daily dosage units of a progestational agent equal in progestational activity to about 35 to about 100 µg levonorgestrel and ethinyl estradiol at a daily dose range of from about 10 to about 35 µg;

b) a second phase of 3 daily dosage units of the antiprogestin of formula I at a daily dose of from about 2 to 50 mg; and c) optionally, a third phase of 4 daily dosage units of an orally and pharmaceutically acceptable placebo.

25. A method of contraception, which comprises administering to a female of child bearing age over a period of 28 consecutive days:

a) a first phase of from 18 to 21 daily dosage units of a progestational agent equal in progestational activity to about 35 to about 150 µg levonorgestrel, and ethinyl estradiol at a daily dose range of from about 10 to about 35 µg;

b) a second phase of from 1 to 7 daily dosage units of a daily dose of from about 2 to 50 mg of an antiprogestin of the formula:

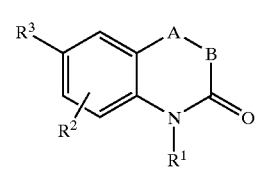

wherein:

$R^1$ is H, OH, $NH_2$, $C_1$ to $C_6$ alkyl, substituted $C_1$ to $C_6$ alkyl, or $COR^A$;

$R^A$ is H, $C_1$ to $C_4$ alkyl, or $C_1$ to $C_4$ alkoxy;

$R^2$ is H, halogen, $NO_2$, $C_1$ to $C_3$ alkyl, or substituted $C_1$ to $C_3$ alkyl;

$R^3$ is the substituted benzene ring having the substituents X and Y:

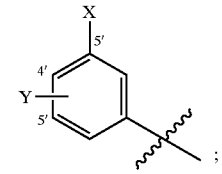

wherein:

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkoxy;

Y is on the 4' or 5' position and is selected from the group consisting of H, halogen, CN, $NO_2$, $C_1$ to $C_3$ alkoxy, $C_1$ to $C_4$ alkyl, and $C_1$ to $C_3$ thioalkoxy;

or a pharmaceutically acceptable salt thereof; and c) optionally, an orally and pharmaceutically acceptable placebo for each remaining day of the 28 consecutive days.

26. A method of contraception, which comprises administering to a female of child bearing age over a period of 28 consecutive days:

a) a first phase of from 18 to 21 daily dosage units of a progestational agent equal in progestational activity to about 35 to about 150 μg levonorgestrel, and ethinyl estradiol at a daily dose range of from about 10 to about 35 μg;

b) a second phase of from 1 to 7 daily dosage units of a daily dose of from about 2 to 50 mg of an antiprogestin of the formula:

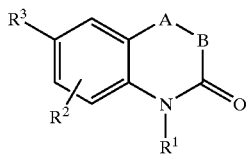

wherein:

A is O, S, or NR$^4$;

B is a bond between A and C=O, or the moiety CR$^5$R$^6$;

R$^4$, R$^5$, and R$^6$ are independently selected from the group consisting of H, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, aryl, substituted aryl, heterocyclic, and substituted heterocyclic;

or R$^4$ and R$^5$ are fused to form a 5 to 7 membered ring;

R$^1$ is selected from the group consisting of H, OH, NH$_2$, C$_1$ to C$_6$ alkyl, substituted C$_1$ to C$_6$ alkyl, C$_3$ to C$_6$ alkenyl, substituted C$_3$ to C$_6$ alkenyl, alkynyl, substituted alkynyl, and COR$^A$;

R$^A$ is selected from the group consisting of H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, and substituted C$_1$ to C$_3$ aminoalkyl;

R$^2$ is selected from the group consisting of H, halogen, CN, NO$_2$, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, and substituted C$_1$ to C$_6$ aminoalkyl;

R$^3$ is the five membered ring of the structure:

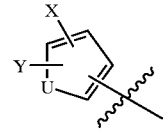

wherein:

U is O, S, or NR$^7$;

X' is selected from the group consisting of halogen, CN, NO$_2$, C$_1$ to C$_3$ alkyl and C$_1$ to C$_3$ alkoxy;

Y' is H or C$_1$ to C$_4$ alkyl;

or a pharmaceutically acceptable salt thereof; and c) optionally, an orally and pharmaceutically acceptable placebo for each remaining day of the 28 consecutive days.

* * * * *

UNITED STATES PATENT AND TRADEMARK OFFICE
CERTIFICATE OF CORRECTION

PATENT NO. : 6,794,373 B2
DATED : September 21, 2004
INVENTOR(S) : Grubb et al.

It is certified that error appears in the above-identified patent and that said Letters Patent is hereby corrected as shown below:

Column 10,
Line 30, replace "from" with -- form --.
Line 67, replace "PR7" with-- R7 --.

Column 13,
Line 2, replace "atorm" with -- atom --.

Column 15,
Line 48, replace "a" with -- an --.

Column 23,
Line 66, replace "(r, 6H)," with -- (m, 6H),--.

Column 24,
Line 41, replace "([M-H], 100%);" with -- ([M-H]-, 100%) --.

Column 25,
Line 8, replace "(nm, 21)," with -- (m, 2H), --.
Line 31, replace "(nm, 3H,)," with -- (m, 3H), --.
Line 45, replace "(M+, 30%);" with -- (M+, 30%); --.

Column 26,
Line 40, replace "[1,2-alquinoxalin-4-one" with -- [1,2-a]quinoxalin-4-one --.

Column 27,
Line 6, replace "filtered off The layers were" with -- filtered off. The layers were --.

Column 28,
Line 21, replace "(7rd, 30 mmol)" with -- (7 ml, 30 mmol) --.

Column 29,
Line 5, replace "(1 •g, 33 mmol)" with -- (11g, 33 mmol) --.
Line 30, replace "(n, 1H)," with -- (m, 1H) --.

UNITED STATES PATENT AND TRADEMARK OFFICE
CERTIFICATE OF CORRECTION

PATENT NO.     : 6,794,373 B2
DATED          : September 21, 2004
INVENTOR(S)    : Grubb et al.

It is certified that error appears in the above-identified patent and that said Letters Patent is hereby corrected as shown below:

Column 30,
Line 33, replace "[M-H]-l." with -- [M-H]- . --.
Line 54, replace "(m, H)," with -- (m, 1H) --.

Column 31,
Line 17, replace "mM" with -- nM --.

Column 34,
Line 6, replace "Approxirately" with -- Approximately --.
Line 49, replace "EC50" with -- EC50 --.

Column 35,
Line 51, replace "medium Cells" with -- medium. Cells --.
Line 52, replace "medium Compounds" with -- medium. Compounds --.

Column 36,
Line 56, replace "100 •g/n streptomycin," with -- 100 •g/ml streptomycin --.

Column 38,
Line 13, replace "-13-dihydro-2H-" with -- 1,3-dihydro-2H --.
Line 21, replace "(in, 2H)," with -- (m, 2H) --.
Line 28, replace ")4-methyl-3,4" with -- )-4-methyl-3,4 --.

Column 39,
Lines 1 and 2, replace "-(H-quinoxalin-2-one 2.4 g, 10 mmol)" with
-- -1H-quinoxalin-2-one (2.4 g, 10 mmol) --.
Line 29, replace "(DMSO-d,)" with -- (DMSO-d6) --.

Column 40,
Line 11, replace "(M-H)-." with -- (M-H)- . --.

Column 41,
Line 35, replace "C to C3 alkyl;" with -- C1 to C3 --.

UNITED STATES PATENT AND TRADEMARK OFFICE
CERTIFICATE OF CORRECTION

PATENT NO.    : 6,794,373 B2
DATED         : September 21, 2004
INVENTOR(S)   : Grubb et al.

It is certified that error appears in the above-identified patent and that said Letters Patent is hereby corrected as shown below:

Column 42,
Line 28, replace "X1 is Nor CX2;" with -- X1 is N or CX2; --.

Signed and Sealed this

Twenty-second Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,794,373 B2
DATED : September 21, 2004
INVENTOR(S) : Grubb et al.

It is certified that error appears in the above-identified patent and that said Letters Patent is hereby corrected as shown below:

Column 10,
Line 30, replace "from" with -- form --.
Line 67, replace "PR7" with -- R7 --.

Column 13,
Line 2, replace "atorm" with -- atom --.

Column 15,
Line 48, replace "a" with -- an --.

Column 23,
Line 66, replace "(r, 6H)," with -- (m, 6H), --.

Column 24,
Line 41, replace "([M-H], 100%);" with -- ([M-H]-, 100%) --.

Column 25,
Line 8, replace "(nm, 21)," with -- (m, 2H), --.
Line 31, replace "(nm, 3H,)," with -- (m, 3H), --.
Line 45, replace "(M+, 30%);" with -- (M+, 30%); --.

Column 26,
Line 40, replace "[1,2-alquinoxalin-4-one" with -- [1,2-a]quinoxalin-4-one --.

Column 27,
Line 6, replace "filtered off The layers were" with -- filtered off. The layers were --.

Column 28,
Line 21, replace "(7rd, 30 mmol)" with -- (7 ml, 30 mmol) --.

Column 29,
Line 5, replace "(1 •g, 33 mmol)" with -- (11g, 33 mmol) --.
Line 30, replace "(n, 1H)," with -- (m, 1H) --.

UNITED STATES PATENT AND TRADEMARK OFFICE
CERTIFICATE OF CORRECTION

PATENT NO. : 6,794,373 B2
DATED : September 21, 2004
INVENTOR(S) : Grubb et al.

It is certified that error appears in the above-identified patent and that said Letters Patent is hereby corrected as shown below:

Column 30,
Line 33, replace "[M-H]-l." with -- [M-H]- . --.
Line 54, replace "(m, H)," with -- (m, 1H) --.

Column 31,
Line 17, replace "mM" with -- nM --.

Column 34,
Line 6, replace "Approxirately" with -- Approximately --.
Line 49, replace "EC50" with -- EC50 --.

Column 35,
Line 51, replace "medium Cells" with -- medium. Cells --.
Line 52, replace "medium Compounds" with -- medium. Compounds --.

Column 36,
Line 56, replace "100 •g/n streptomycin," with -- 100 •$\mu$g/ml streptomycin --.

Column 38,
Line 13, replace "-13-dihydro-2H-" with -- 1,3-dihydro-2H --.
Line 21, replace "(in, 2H)," with -- (m, 2H) --.
Line 28, replace ")4-methyl-3,4" with -- )-4-methyl-3,4 --.

Column 39,
Lines 1 and 2, replace "-(H-quinoxalin-2-one 2.4 g, 10 mmol)" with
-- -1H-quinoxalin-2-one (2.4 g, 10 mmol) --.
Line 29, replace "(DMSO-d,)" with -- (DMSO-d6) --.

Column 40,
Line 11, replace "(M-H)-." with -- (M-H)- . --.

Column 41,
Line 35, replace "C to C3 alkyl;" with -- C1 to C3 --.

UNITED STATES PATENT AND TRADEMARK OFFICE
CERTIFICATE OF CORRECTION

PATENT NO. : 6,794,373 B2
DATED : September 21, 2004
INVENTOR(S) : Grubb et al.

It is certified that error appears in the above-identified patent and that said Letters Patent is hereby corrected as shown below:

<u>Column 42,</u>
Line 28, replace "X1 is Nor CX2;" with -- X1 is N or CX2; --.

This certificate supersedes Certificate of Correction issued February 22, 2005.

Signed and Sealed this

Twenty-eighth Day of June, 2005

JON W. DUDAS
*Director of the United States Patent and Trademark Office*